(12) United States Patent
Klockmann et al.

(10) Patent No.: US 9,617,287 B2
(45) Date of Patent: *Apr. 11, 2017

(54) MERCAPTOSILANES

(75) Inventors: Oliver Klockmann, Niederzier (DE);
Philipp Albert, Lörrach (DE); Andre Hasse, Linnich (DE); Karsten Korth, Grenzach-Wyhlen (DE); Relmund Pieter, Bensheim (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/196,232

(22) Filed: Aug. 2, 2011

(65) Prior Publication Data

US 2011/0287205 A1   Nov. 24, 2011

Related U.S. Application Data

(62) Division of application No. 11/337,205, filed on Jan. 20, 2006, now Pat. No. 8,013,178.

(30) Foreign Application Priority Data

Jan. 20, 2005  (DE) .................. 10 2005 002 575
Jul. 13, 2005   (DE) .................. 10 2005 032 658
Dec. 3, 2005   (DE) .................. 10 2005 057 801

(51) Int. Cl.
| | | |
|---|---|---|
| B32B 1/08 | (2006.01) | |
| C07F 7/18 | (2006.01) | |
| A43B 13/02 | (2006.01) | |
| C08L 9/00 | (2006.01) | |
| C08K 5/548 | (2006.01) | |

(52) U.S. Cl.
CPC ............ C07F 7/1836 (2013.01); C08K 5/548 (2013.01); Y10T 428/139 (2015.01)

(58) Field of Classification Search
None
See application file for complete search history.

(56) References Cited

U.S. PATENT DOCUMENTS

| 6,849,754 | B2 | 2/2005 | Deschler et al. | |
| 7,384,997 | B2 * | 6/2008 | Hasse et al. | 524/262 |
| 8,013,178 | B2 * | 9/2011 | Klockmann et al. | 556/427 |

FOREIGN PATENT DOCUMENTS

| DE | 2 255 577 | 6/1974 |
| DE | 34 26 987 A1 | 1/1986 |
| DE | 34 26 987 A1 | 1/1988 |
| DE | 101 37 809 | 8/2001 |
| DE | 100 15 309 A1 | 10/2001 |
| DE | 101 63 941 | 12/2001 |
| DE | 102 23 658 A1 | 12/2003 |
| DE | 103 27 624 B3 | 12/2004 |
| EP | 0 085 831 A2 | 8/1983 |
| EP | 1 285 926 A1 | 2/2003 |
| EP | 1 394 166 A2 | 3/2004 |
| EP | 1 394 168 A2 | 3/2004 |
| EP | 1 439 205 A1 | 7/2004 |
| EP | 1 634 884 A1 | 3/2006 |
| EP | 1 637 535 A1 | 3/2006 |
| JP | 62-181346 A2 | 5/1987 |
| JP | 62-181346 | 8/1987 |
| JP | 62-181346 A2 | 8/1987 |
| JP | 2005-232445 A2 | 1/2005 |

OTHER PUBLICATIONS

U.S. Appl. No. 12/309,703, filed Jan. 27, 2009.*
F.D. Osterholtz; Kinetics of the Hydrolysis and condensation of organofunctional alkoxysilanes: a review; J. Adhesion Sci. Technot., vol. 6, No. 1, pp. 127-149 (1992).
O. Klocmannn, et al;. A New Silane for Future Requirements—Lower Rolling Resistance, Lower VOCs; Rubber World, Aug. 2006; pp. 26-40.
Plueddemann, Edwin P., "Silane Coupling Agents, Second Edition," 1991, entire document, Dow Corning Corporation, Midland, Michigan.

* cited by examiner

Primary Examiner — Rosalynd Keys
(74) Attorney, Agent, or Firm — Smith, Gambrell & Russell, LLP

(57) ABSTRACT

Mercaptosilanes are disclosed of the formula I

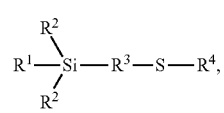

wherein $R^1$ is an alkyl polyether group $—O—(R^5—O)_m—R^6$. They are prepared by a procedure in which a silane of the formula II

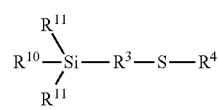

is subjected to a catalyzed reaction with an alkyl polyether $R^1—H$, $R^7—OH$ being split off, the molar ratio of the alkyl polyethers $R^1—H$ to the silane of the formula II is at least 0.5 and $R^7—OH$ is separated off from the reaction mixture continuously or discontinuously. They can be used in shaped articles.

21 Claims, No Drawings

MERCAPTOSILANES

This application is a divisional of U.S. patent application Ser. No. 11/337,205, filed 20 Jan. 2006, now U.S. Pat. No. 8,013,178 which is herein incorporated by reference in its entirety.

The invention relates to mercaptosilanes, a process for their preparation and their use.

It is known to employ silanes as adhesion promoters. Thus, aminoalkyltrialkoxysilanes, methacryloxyalkyltrialkoxysilanes, polysulfanalkyltrialkoxysilanes and mercaptoalkyltrialkoxysilanes are employed as adhesion promoters between inorganic materials and organic polymers, as crosslinking agents and as surface-modifying agents (E. P. Plueddemann, "Silane Coupling Agents", 2nd ed. Plenum Press 1982).

These adhesion promoters or coupling or bonding agents form bonds both to the filler and to the elastomer and thus effect a good interaction between the filler surface and the elastomer.

It is furthermore known that the use of commercially available silane adhesion promoters (DE 22 55 577) having three alkoxy substituents on the silicon atom leads to the release of considerable amounts of alcohol during and after the binding to the filler. Since as a rule trimethoxy- and triethoxy-substituted silanes are employed, the corresponding alcohols, methanol and ethanol, are released in considerable amounts.

It is furthermore known from DE 10015309 that the use of a mercaptosilane in combination with a long-chain alkylsilane leads to rubber mixtures of increased amplification ratio and reduced hysteresis loss. The alkylsilane is necessary in order to ensure a reliable processability of the rubber mixture.

It is furthermore known that methoxy- and ethoxy-substituted silanes are more reactive than the corresponding long-chain alkoxy-substituted silanes and can thus bind to the filler more rapidly, so that from the technical and economic aspect it has not hitherto been possible to dispense with the use of methoxy and ethoxy substituents.

Silanes, such as are known from DE 10327624, which are substituted completely by long-chain alkoxy groups only show a balanced profile of rubber values if an adequate minimum mixing time is ensured.

DE 10137809 discloses organosilicon compounds of the general formulae

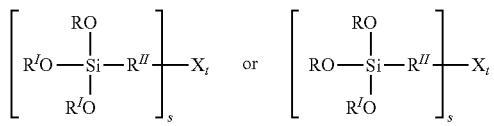

wherein R is a methyl or ethyl group,
$R^I$ is identical or different and is a $C_9$-$C_{30}$ branched or unbranched monovalent alkyl or alkenyl group, aryl group, aralkyl group, branched or unbranched $C_2$-$C_{30}$ alkyl ether group, branched or unbranched $C_2$-$C_{30}$ alkyl polyether group,
X is $NH_{(3-s)}$, $O(C=O)$—$R^{III}$, SH, S, $S(C=O)$—$R^{III}$ or H.

JP 62-181346 discloses rubber mixtures which contain carbon black as a filler and comprise silanes of the formula $HS$—$(CH_2)_3$—$Si$—$(OR_1)_n(OCH_3)_{3-n}$.

DE 10223658 discloses organosilicon compounds of the general formulae

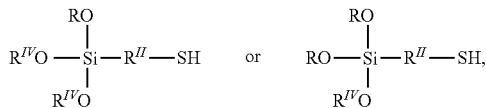

wherein $R^{IV}$ is identical or different and is a $C_9$-$C_{30}$ branched or unbranched monovalent alkyl group,
$R^{IV}$ is a mixture and the content of one component of the mixture is 10 to 50 mol %,
which, without the addition of alkylsilanes, also lead to rubber mixtures having an increased amplification ratio and a reduced hysteresis loss, with at the same time an ensured processability of the rubber mixture.

DE 3426987 discloses organosilicon compounds of the general formula

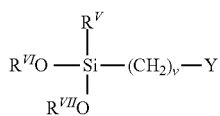

where Y=—SH or $NHR^{VIII}$, $R^V$=—$CH_3$, —$C_2H_5$ or $OR^{VI}$, $R^{VI}$=($CH_2$—$CH_2$—O)$_w$—$R^{IX}$, $R^{VII}$=alkyl radical having 1-4 C atoms or $R^{VI}$, $R^{IX}$=optionally substituted alkyl or aryl radical having 1-10 C atoms,
which are used for the preparation of storage-stable synthetic resin compositions.

EP 0085831 discloses organosilicon compounds of the general formula $$A\text{-}(CH_2)_h\text{—}Si(CH_3)_iB_kQ_{3-(i+k)},$$

in which A represents a radical from the group consisting of $NHR^X$, —SH, —O—CH(O)CH$_2$ or —NH—(CH$_2$)$_2$—NH—(CH$_2$)$_2$—NH$_2$,
B represents a radical from the group consisting of —OCH$_3$, —OC$_2$H$_5$ and —OC$_3$H$_7$,
Q represents the radical —O—(CH$_2$—CH$_2$—O)$_l$—R$^{XI}$, wherein one of the H atoms can be replaced by a methyl group, l can assume the values 2 or 3 and R$^{XI}$ represents an alkyl radical having 1 to 4 C atoms,
which are employed in polyurethane sealing compositions.

A disadvantage of the known mercaptosilanes having long-chain alkoxy groups is their low reactivity in respect of coupling to the silica. The high amplification ratio achieved in rubber mixtures by the addition of mercaptosilanes, the low hysteresis loss and the high abrasion resistance are only achieved if a sufficient mixing time is ensured. From the economic and technical aspect, however, a short mixing time is indispensable, so that it has not hitherto been possible to dispense with the use of mercaptosilanes substituted completely by methoxy and/or ethoxy groups.

The object of the present invention is to provide mercaptosilanes which, with economically acceptable, short mixing times and ensured processing, also lead to a high amplification ratio, a low hysteresis loss and a high abrasion resistance, with at the same time a reduced emission of alcohol compared with trimethoxy- and triethoxy-substituted mercaptosilanes.

The invention provides mercaptosilanes of the general formula I

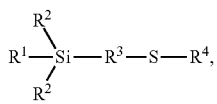

wherein $R^1$ is an alkyl polyether group —O—($R^5$—O)$_m$—$R^6$, where
$R^5$ is identical or different and is a branched or unbranched, saturated or unsaturated, aliphatic divalent C1-C30 hydrocarbon group, preferably CH$_2$—CH$_2$, CH$_2$—CH(CH$_3$), —CH(CH$_3$)—CH$_2$—, CH$_2$—CH$_2$—CH$_2$ or mixtures thereof, m is on average 1 to 30, preferably 2 to 20, particularly preferably 2 to 15, very particularly preferably 3 to 10, and exceptionally preferably 3.5 to 7.9, and $R^6$ comprises at least 11, preferably at least 12 C atoms and is an unsubstituted or substituted, branched or unbranched monovalent alkyl, alkenyl, aryl or aralkyl group,
$R^2$ is identical or different and is an $R^1$, C1-C12 alkyl or $R^7$O group, where $R^7$ is H, methyl, ethyl, propyl, a C9-C30 branched or unbranched monovalent alkyl, alkenyl, aryl or aralkyl group or ($R^8$)$_3$Si group, where $R^8$ is a C1-C30 branched or unbranched alkyl or alkenyl group,
$R^3$ is a branched or unbranched, saturated or unsaturated, aliphatic, aromatic or mixed aliphatic/aromatic divalent C1-C30 hydrocarbon group and
$R^4$ is H, CN or (C=O)—$R^9$, where $R^9$ is a branched or unbranched, saturated or unsaturated, aliphatic, aromatic or mixed aliphatic/aromatic monovalent C1-C30, preferably C5 to C30, particularly preferably C5 to C20, very particularly preferably C7 to C15, exceptionally preferably C7 to C11 hydrocarbon group.

The mercaptosilane of the general formula I can be a mixture of various mercaptosilanes of the general formula I or condensation products thereof.

The mercaptosilanes of the general formula I can be compounds wherein $R^1$ is an alkyl polyether group —O—($R^5$—O)$_m$—$R^6$, where $R^5$ is identical or different and is a branched or unbranched, saturated or unsaturated, aliphatic divalent C1-C30 hydrocarbon group, m is on average 1 to 30, and $R^6$ comprises at least 11 C atoms and is an unsubstituted or substituted, branched or unbranched monovalent alkyl, alkenyl, aryl or aralkyl group,
$R^2$ is identical and is a C1-C12 alkyl or $R^7$O group, where $R^7$ is H, ethyl, propyl, a C9-C30 branched or unbranched monovalent alkyl, alkenyl, aryl or aralkyl group or ($R^8$)$_3$Si group, where $R^8$ is a C1-C30 branched or unbranched alkyl or alkenyl group,
$R^3$ is a branched or unbranched, saturated or unsaturated, aliphatic, aromatic or mixed aliphatic/aromatic divalent C1-C30 hydrocarbon group and
$R^4$ is H, CN or (C=O)—$R^9$, where $R^9$ is a branched or unbranched, saturated or unsaturated, aliphatic, aromatic or mixed aliphatic/aromatic monovalent C1-C30 hydrocarbon group.

The mercaptosilanes of the general formula I can be compounds wherein $R^1$ is
—O—(C$_2$H$_4$—O)$_5$—C$_{11}$H$_{23}$, —O—(C$_2$H$_4$—O)$_5$—C$_{12}$H$_{25}$, —O—(C$_2$H$_4$—O)$_5$—C$_{13}$H$_{27}$, —O—(C$_2$H$_4$—O)$_5$—C$_{14}$H$_{29}$, —O—(C$_2$H$_4$—O)$_5$—C$_{15}$H$_{31}$, —O—(C$_2$H$_4$—O)$_3$—C$_{13}$H$_{27}$, —O—(C$_2$H$_4$—O)$_4$—C$_{13}$H$_{27}$, —O—(C$_2$H$_4$—O)$_6$—C$_{13}$H$_{27}$, —O—(C$_2$H$_4$—O)$_7$—C$_{13}$H$_{27}$, —O—(CH$_2$CH$_2$—O)$_5$—(CH$_2$)$_{10}$CH$_3$, —O—(CH$_2$CH$_2$—O)$_5$—(CH$_2$)$_{11}$CH$_3$, —O—(CH$_2$CH$_2$—O)$_5$—(CH$_2$)$_{12}$CH$_3$, —O—(CH$_2$CH$_2$—O)$_5$—(CH$_2$)$_{13}$CH$_3$, —O—(CH$_2$CH$_2$—O)$_5$—(CH$_2$)$_{14}$CH$_3$, —O—(CH$_2$CH$_2$—O)$_3$—(CH$_2$)$_{12}$CH$_3$, —O—(CH$_2$CH$_2$—O)$_4$—(CH$_2$)$_{12}$CH$_3$, —O—(CH$_2$CH$_2$—O)$_6$—(CH$_2$)$_{12}$CH$_3$, —O—(CH$_2$CH$_2$—O)$_7$—(CH$_2$)$_{12}$CH$_3$,

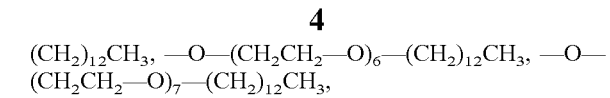

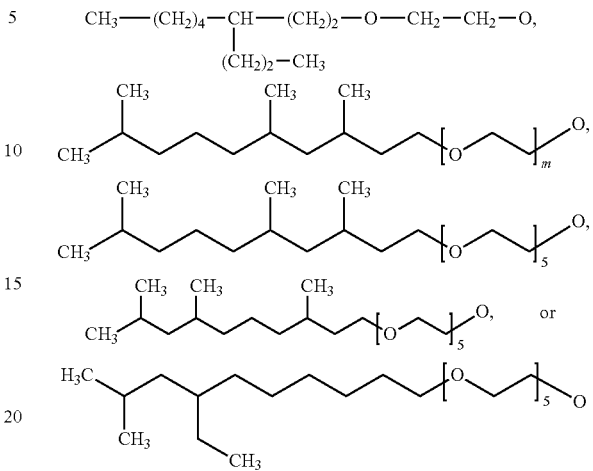

$R^2$ is different and is an $R^1$, C1-C12 alkyl or $R^7$O group, where $R^7$ is H, methyl, ethyl, propyl, a C9-C30 branched or unbranched monovalent alkyl, alkenyl, aryl or aralkyl group or ($R^8$)$_3$Si group, where $R^8$ is a C1-C30 branched or unbranched alkyl or alkenyl group,
$R^3$ is a branched or unbranched, saturated or unsaturated, aliphatic, aromatic or mixed aliphatic/aromatic divalent C1-C30 hydrocarbon group and
$R^4$ is H, CN or (C=O)—$R^9$, where $R^9$ is a branched or unbranched, saturated or unsaturated, aliphatic, aromatic or mixed aliphatic/aromatic monovalent C$_1$-C30 hydrocarbon group.

The mercaptosilanes of the general formula I can be compounds wherein $R^1$ is
—O—(C$_2$H$_4$—O)$_5$—C$_{11}$H$_{23}$, —O—(C$_2$H$_4$—O)$_5$—C$_{12}$H$_{25}$, —O—(C$_2$H$_4$—O)$_5$—C$_{13}$H$_{27}$, —O—(C$_2$H$_4$—O)$_5$—C$_{14}$H$_{29}$, —O—(C$_2$H$_4$—O)$_5$—C$_{15}$H$_{31}$, —O—(C$_2$H$_4$—O)$_3$—C$_{13}$H$_{27}$, —O—(C$_2$H$_4$—O)$_4$—C$_{13}$H$_{27}$, —O—(C$_2$H$_4$—O)$_6$—C$_{13}$H$_{27}$, —O—(C$_2$H$_4$—O)$_7$—C$_{13}$H$_{27}$, —O—(CH$_2$CH$_2$—O)$_5$—(CH$_2$)$_{10}$CH$_3$, —O—(CH$_2$CH$_2$—O)$_5$—(CH$_2$)$_{11}$CH$_3$, —O—(CH$_2$CH$_2$—O)$_5$—(CH$_2$)$_{12}$CH$_3$, —O—(CH$_2$CH$_2$—O)$_5$—(CH$_2$)$_{13}$CH$_3$, —O—(CH$_2$CH$_2$—O)$_5$—(CH$_2$)$_{14}$CH$_3$, —O—(CH$_2$CH$_2$—O)$_3$—(CH$_2$)$_{12}$CH$_3$, —O—(CH$_2$CH$_2$—O)$_4$—(CH$_2$)$_{12}$CH$_3$, —O—(CH$_2$CH$_2$—O)$_6$—(CH$_2$)$_{12}$CH$_3$, —O—(CH$_2$CH$_2$—O)$_7$—(CH$_2$)$_{12}$CH$_3$, $R^2$ is an $R^1$ group,
$R^3$ is a branched or unbranched, saturated or unsaturated, aliphatic, aromatic or mixed aliphatic/aromatic divalent C1-C30 hydrocarbon group and
$R^4$ is H, CN or (C=O)—$R^9$, where $R^9$ is a branched or unbranched, saturated or unsaturated, aliphatic, aromatic or mixed aliphatic/aromatic monovalent C1-C30 hydrocarbon group.

Preferred compounds of the formula I where $R^4$=H can be:

$[(C_{11}H_{23}O-(CH_2-CH_2O)_2](EtO)_2Si(CH_2)_3SH$,
$[(C_{11}H_{23}O-(CH_2-CH_2O)_3](EtO)_2Si(CH_2)_3SH$,
$[(C_{11}H_{23}O-(CH_2-CH_2O)_4](EtO)_2Si(CH_2)_3SH$,
$[(C_{11}H_{23}O-(CH_2-CH_2O)_5](EtO)_2Si(CH_2)_3SH$,
$[(C_{11}H_{23}O-(CH_2-CH_2O)_6](EtO)_2Si(CH_2)_3SH$,
$[(C_{12}H_{25}O-(CH_2-CH_2O)_2](EtO)_2Si(CH_2)_3SH$,
$[(C_{12}H_{25}O-(CH_2-CH_2O)_3](EtO)_2Si(CH_2)_3SH$,
$[(C_{12}H_{25}O-(CH_2-CH_2O)_4](EtO)_2Si(CH_2)_3SH$,
$[(C_{12}H_{25}O-(CH_2-CH_2O)_5](EtO)_2Si(CH_2)_3SH$,
$[(C_{12}H_{25}O-(CH_2-CH_2O)_6](EtO)_2Si(CH_2)_3SH$,
$[(C_{13}H_{27}O-(CH_2-CH_2O)_2](EtO)_2Si(CH_2)_3SH$,
$[(C_{13}H_{27}O-(CH_2-CH_2O)_3](EtO)_2Si(CH_2)_3SH$,
$[(C_{13}H_{27}O-(CH_2-CH_2O)_4](EtO)_2Si(CH_2)_3SH$,
$[(C_{13}H_{27}O-(CH_2-CH_2O)_5](EtO)_2Si(CH_2)_3SH$,
$[(C_{13}H_{27}O-(CH_2-CH_2O)_6](EtO)_2Si(CH_2)_3SH$,
$[(C_{14}H_{29}O-(CH_2-CH_2O)_2](EtO)_2Si(CH_2)_3SH$,
$[(C_{14}H_{29}O-(CH_2-CH_2O)_3](EtO)_2Si(CH_2)_3SH$,
$[(C_{14}H_{29}O-(CH_2-CH_2O)_4](EtO)_2Si(CH_2)_3SH$,
$[(C_{14}H_{29}O-(CH_2-CH_2O)_5](EtO)_2Si(CH_2)_3SH$,
$[(C_{14}H_{29}O-(CH_2-CH_2O)_6](EtO)_2Si(CH_2)_3SH$,
$[(C_{15}H_{31}O-(CH_2-CH_2O)_2](EtO)_2Si(CH_2)_3SH$,
$[(C_{15}H_{31}O-(CH_2-CH_2O)_3](EtO)_2Si(CH_2)_3SH$,
$[(C_{15}H_{31}O-(CH_2-CH_2O)_4](EtO)_2Si(CH_2)_3SH$,
$[(C_{15}H_{31}O-(CH_2-CH_2O)_5](EtO)_2Si(CH_2)_3SH$,
$[(C_{15}H_{31}O-(CH_2-CH_2O)_6](EtO)_2Si(CH_2)_3SH$,
$[(C_{16}H_{33}O-(CH_2-CH_2O)_2](EtO)_2Si(CH_2)_3SH$,
$[(C_{16}H_{33}O-(CH_2-CH_2O)_3](EtO)_2Si(CH_2)_3SH$,
$[(C_{16}H_{33}O-(CH_2-CH_2O)_4](EtO)_2Si(CH_2)_3SH$,
$[(C_{16}H_{33}O-(CH_2-CH_2O)_5](EtO)_2Si(CH_2)_3SH$,
$[(C_{16}H_{33}O-(CH_2-CH_2O)_6](EtO)_2Si(CH_2)_3SH$,
$[(C_{17}H_{35}O-(CH_2-CH_2O)_2](EtO)_2Si(CH_2)_3SH$,
$[(C_{17}H_{35}O-(CH_2-CH_2O)_3](EtO)_2Si(CH_2)_3SH$,
$[(C_{17}H_{35}O-(CH_2-CH_2O)_4](EtO)_2Si(CH_2)_3SH$,
$[(C_{17}H_{35}O-(CH_2-CH_2O)_5](EtO)_2Si(CH_2)_3SH$,
$[(C_{17}H_{35}O-(CH_2-CH_2O)_6](EtO)_2Si(CH_2)_3SH$,
$[(C_{11}H_{23}O-(CH_2-CH_2O)_2]_2(EtO)_2Si(CH_2)_3SH$,
$[(C_{11}H_{23}O-(CH_2-CH_2O)_3]_2(EtO)_2Si(CH_2)_3SH$,
$[(C_{11}H_{23}O-(CH_2-CH_2O)_4]_2(EtO)_2Si(CH_2)_3SH$,
$[(C_{11}H_{23}O-(CH_2-CH_2O)_5]_2(EtO)_2Si(CH_2)_3SH$,
$[(C_{11}H_{23}O-(CH_2-CH_2O)_6]_2(EtO)_2Si(CH_2)_3SH$,
$[(C_{12}H_{25}O-(CH_2-CH_2O)_2]_2(EtO)_2Si(CH_2)_3SH$,
$[(C_{12}H_{25}O-(CH_2-CH_2O)_3]_2(EtO)_2Si(CH_2)_3SH$,
$[(C_{12}H_{25}O-(CH_2-CH_2O)_4]_2(EtO)_2Si(CH_2)_3SH$,
$[(C_{12}H_{25}O-(CH_2-CH_2O)_5]_2(EtO)_2Si(CH_2)_3SH$,
$[(C_{12}H_{25}O-(CH_2-CH_2O)_6]_2(EtO)_2Si(CH_2)_3SH$,
$[(C_{13}H_{27}O-(CH_2-CH_2O)_2]_2(EtO)_2Si(CH_2)_3SH$,
$[(C_{13}H_{27}O-(CH_2-CH_2O)_3]_2(EtO)_2Si(CH_2)_3SH$,
$[(C_{13}H_{27}O-(CH_2-CH_2O)_4]_2(EtO)_2Si(CH_2)_3SH$,
$[(C_{13}H_{27}O-(CH_2-CH_2O)_5]_2(EtO)_2Si(CH_2)_3SH$,
$[(C_{13}H_{27}O-(CH_2-CH_2O)_6]_2(EtO)_2Si(CH_2)_3SH$,
$[(C_{14}H_{29}O-(CH_2-CH_2O)_2]_2(EtO)Si(CH_2)_3SH$,
$[(C_{14}H_{29}O-(CH_2-CH_2O)_3]_2(EtO)Si(CH_2)_3SH$,
$[(C_{14}H_{29}O-(CH_2-CH_2O)_4]_2(EtO)Si(CH_2)_3SH$,
$[(C_{14}H_{29}O-(CH_2-CH_2O)_5]_2(EtO)Si(CH_2)_3SH$,
$[(C_{14}H_{29}O-(CH_2-CH_2O)_6]_2(EtO)Si(CH_2)_3SH$,
$[(C_{15}H_{31}O-(CH_2-CH_2O)_2]_2(EtO)Si(CH_2)_3SH$,
$[(C_{15}H_{31}O-(CH_2-CH_2O)_3]_2(EtO)Si(CH_2)_3SH$,
$[(C_{15}H_{31}O-(CH_2-CH_2O)_4]_2(EtO)Si(CH_2)_3SH$,
$[(C_{15}H_{31}O-(CH_2-CH_2O)_5]_2(EtO)Si(CH_2)_3SH$,
$[(C_{15}H_{31}O-(CH_2-CH_2O)_6]_2(EtO)Si(CH_2)_3SH$,
$[(C_{16}H_{33}O-(CH_2-CH_2O)_2]_2(EtO)Si(CH_2)_3SH$,
$[(C_{16}H_{33}O-(CH_2-CH_2O)_3]_2(EtO)Si(CH_2)_3SH$,
$[(C_{16}H_{33}O-(CH_2-CH_2O)_4]_2(EtO)Si(CH_2)_3SH$,
$[(C_{16}H_{33}O-(CH_2-CH_2O)_5]_2(EtO)Si(CH_2)_3SH$,
$[(C_{16}H_{33}O-(CH_2-CH_2O)_6]_2(EtO)Si(CH_2)_3SH$,
$[(C_{17}H_{35}O-(CH_2-CH_2O)_2]_2(EtO)Si(CH_2)_3SH$,
$[(C_{17}H_{35}O-(CH_2-CH_2O)_3]_2(EtO)Si(CH_2)_3SH$,
$[(C_{17}H_{35}O-(CH_2-CH_2O)_4]_2(EtO)Si(CH_2)_3SH$,
$[(C_{17}H_{35}O-(CH_2-CH_2O)_5]_2(EtO)Si(CH_2)_3SH$,
$[(C_{17}H_{35}O-(CH_2-CH_2O)_6]_2(EtO)Si(CH_2)_3SH$,
$[(C_{11}H_{23}O-(CH_2-CH_2O)_2]_3Si(CH_2)_3SH$,
$[(C_{11}H_{23}O-(CH_2-CH_2O)_3]_3Si(CH_2)_3SH$,
$[(C_{11}H_{23}O-(CH_2-CH_2O)_4]_3Si(CH_2)_3SH$,
$[(C_{11}H_{23}O-(CH_2-CH_2O)_5]_3Si(CH_2)_3SH$,
$[(C_{11}H_{23}O-(CH_2-CH_2O)_6]_3Si(CH_2)_3SH$,
$[(C_{12}H_{25}O-(CH_2-CH_2O)_2]_3Si(CH_2)_3SH$,
$[(C_{12}H_{25}O-(CH_2-CH_2O)_3]_3Si(CH_2)_3SH$,
$[(C_{12}H_{25}O-(CH_2-CH_2O)_4]_3Si(CH_2)_3SH$,
$[(C_{12}H_{25}O-(CH_2-CH_2O)_5]_3Si(CH_2)_3SH$,
$[(C_{12}H_{25}O-(CH_2-CH_2O)_6]_3Si(CH_2)_3SH$,
$[(C_{13}H_{27}O-(CH_2-CH_2O)_2]_3Si(CH_2)_3SH$,
$[(C_{13}H_{27}O-(CH_2-CH_2O)_3]_3Si(CH_2)_3SH$,
$[(C_{13}H_{27}O-(CH_2-CH_2O)_4]_3Si(CH_2)_3SH$,
$[(C_{13}H_{27}O-(CH_2-CH_2O)_5]_3Si(CH_2)_3SH$,
$[(C_{13}H_{27}O-(CH_2-CH_2O)_6]_3Si(CH_2)_3SH$,
$[(C_{14}H_{29}O-(CH_2-CH_2O)_2]_3Si(CH_2)_3SH$,
$[(C_{14}H_{29}O-(CH_2-CH_2O)_3]_3Si(CH_2)_3SH$,
$[(C_{14}H_{29}O-(CH_2-CH_2O)_4]_3Si(CH_2)_3SH$,
$[(C_{14}H_{29}O-(CH_2-CH_2O)_5]_3Si(CH_2)_3SH$,
$[(C_{14}H_{29}O-(CH_2-CH_2O)_6]_3Si(CH_2)_3SH$,
$[(C_{15}H_{31}O-(CH_2-CH_2O)_2]_3Si(CH_2)_3SH$,
$[(C_{15}H_{31}-(CH_2-CH_2O)_3]_3Si(CH_2)_3SH$,
$[(C_{15}H_{31}O-(CH_2-CH_2O)_4]_3Si(CH_2)_3SH$,
$[(C_{15}H_{31}O-(CH_2-CH_2O)_5]_3Si(CH_2)_3SH$,
$[(C_{15}H_{31}O-(CH_2-CH_2O)_6]_3Si(CH_2)_3SH$,
$[(C_{16}H_{33}O-(CH_2-CH_2O)_2]_3Si(CH_2)_3SH$,
$[(C_{16}H_{33}-(CH_2-CH_2O)_3]_3Si(CH_2)_3SH$,
$[(C_{16}H_{33}O-(CH_2-CH_2O)_4]_3Si(CH_2)_3SH$,
$[(C_{16}H_{33}O-(CH_2-CH_2O)_5]_3Si(CH_2)_3SH$,
$[(C_{16}H_{33}O-(CH_2-CH_2O)_6]_3Si(CH_2)_3SH$,
$[(C_{17}H_{35}O-(CH_2-CH_2O)_2]_3Si(CH_2)_3SH$,
$[(C_{17}H_{35}-(CH_2-CH_2O)_3]_3Si(CH_2)_3SH$,
$[(C_{17}H_{35}O-(CH_2-CH_2O)_4]_3Si(CH_2)_3SH$,
$[(C_{17}H_{35}O-(CH_2-CH_2O)_5]_3Si(CH_2)_3SH$,
$[(C_{17}H_{35}O-(CH_2-CH_2O)_6]_3Si(CH_2)_3SH$,
$[(C_{11}H_{23}O-(CH_2-CH_2O)_2](EtO)_2Si-CH_2-CH(CH_3)-CH_2-SH$,
$[(C_{11}H_{23}O-(CH_2-CH_2O)_3](EtO)_2Si-CH_2-CH(CH_3)-CH_2-SH$,
$[(C_{11}H_{23}O-(CH_2-CH_2O)_4](EtO)_2Si-CH_2-CH(CH_3)-CH_2-SH$,
$[(C_{11}H_{23}O-(CH_2-CH_2O)_5](EtO)_2Si-CH_2-CH(CH_3)-CH_2-SH$,
$[(C_{11}H_{23}O-(CH_2-CH_2O)_6](EtO)_2Si-CH_2-CH(CH_3)-CH_2-SH$,
$[(C_{12}H_{25}O-(CH_2-CH_2O)_2](EtO)_2Si-CH_2-CH(CH_3)-CH_2-SH$,

[(C₁₂H₂₅O—(CH₂—CH₂O)₃](EtO)₂Si—CH₂—CH(CH₃)—CH₂—SH,
[(C₁₂H₂₅O—(CH₂—CH₂O)₄](EtO)₂Si—CH₂—CH(CH₃)—CH₂—SH,
[(C₁₂H₂₅O—(CH₂—CH₂O)₅](EtO)₂Si—CH₂—CH(CH₃)—CH₂—SH,
[(C₁₂H₂₅O—(CH₂—CH₂O)₆](EtO)₂Si—CH₂—CH(CH₃)—CH₂—SH,
[(C₁₃H₂₇O—(CH₂—CH₂O)₂](EtO)₂Si—CH₂—CH(CH₃)—CH₂—SH,
[(C₁₃H₂₇O—(CH₂—CH₂O)₃](EtO)₂Si—CH₂—CH(CH₃)—CH₂—SH,
[(C₁₃H₂₇O—(CH₂—CH₂O)₄](EtO)₂Si—CH₂—CH(CH₃)—CH₂—SH,
[(C₁₃H₂₇O—(CH₂—CH₂O)₅](EtO)₂Si—CH₂—CH(CH₃)—CH₂—SH,
[(C₁₃H₂₇O—(CH₂—CH₂O)₆](EtO)₂Si—CH₂—CH(CH₃)—CH₂—SH,
[(C₁₄H₂₉O—(CH₂—CH₂O)₂](EtO)₂Si—CH₂—CH(CH₃)—CH₂—SH,
[(C₁₄H₂₉O—(CH₂—CH₂O)₃](EtO)₂Si—CH₂—CH(CH₃)—CH₂—SH,
[(C₁₄H₂₉O—(CH₂—CH₂O)₄](EtO)₂Si—CH₂—CH(CH₃)—CH₂—SH,
[(C₁₄H₂₉O—(CH₂—CH₂O)₅](EtO)₂Si—CH₂—CH(CH₃)—CH₂—SH,
[(C₁₄H₂₉O—(CH₂—CH₂O)₆](EtO)₂Si—CH₂—CH(CH₃)—CH₂—SH,
[(C₁₅H₃₁O—(CH₂—CH₂O)₂](EtO)₂Si—CH₂—CH(CH₃)—CH₂—SH,
[(C₁₅H₃₁O—(CH₂—CH₂O)₃](EtO)₂Si—CH₂—CH(CH₃)—CH₂—SH,
[(C₁₅H₃₁O—(CH₂—CH₂O)₄](EtO)₂Si—CH₂—CH(CH₃)—CH₂—SH,
[(C₁₅H₃₁O—(CH₂—CH₂O)₅](EtO)₂Si—CH₂—CH(CH₃)—CH₂—SH,
[(C₁₅H₃₁O—(CH₂—CH₂O)₆](EtO)₂Si—CH₂—CH(CH₃)—CH₂—SH,
[(C₁₆H₃₃O—(CH₂—CH₂O)₂](EtO)₂Si—CH₂—CH(CH₃)—CH₂—SH,
[(C₁₆H₃₃O—(CH₂—CH₂O)₃](EtO)₂Si—CH₂—CH(CH₃)—CH₂—SH,
[(C₁₆H₃₃O—(CH₂—CH₂O)₄](EtO)₂Si—CH₂—CH(CH₃)—CH₂—SH,
[(C₁₆H₃₃O—(CH₂—CH₂O)₅](EtO)₂Si—CH₂—CH(CH₃)—CH₂—SH,
[(C₁₆H₃₃O—(CH₂—CH₂O)₆](EtO)₂Si—CH₂—CH(CH₃)—CH₂—SH,
[(C₁₇H₃₅O—(CH₂—CH₂O)₂](EtO)₂Si—CH₂—CH(CH₃)—CH₂—SH,
[(C₁₇H₃₅O—(CH₂—CH₂O)₃](EtO)₂Si—CH₂—CH(CH₃)—CH₂—SH,
[(C₁₇H₃₅O—(CH₂—CH₂O)₄](EtO)₂Si—CH₂—CH(CH₃)—CH₂—SH,
[(C₁₇H₃₅O—(CH₂—CH₂O)₅](EtO)₂Si—CH₂—CH(CH₃)—CH₂—SH,
[(C₁₇H₃₅O—(CH₂—CH₂O)₆](EtO)₂Si—CH₂—CH(CH₃)—CH₂—SH,
[(C₁₁H₂₃O—(CH₂—CH₂O)₂]₂(EtO)Si—CH₂—CH(CH₃)—CH₂—SH,
[(C₁₁H₂₃O—(CH₂—CH₂O)₃]₂(EtO)Si—CH₂—CH(CH₃)—CH₂—SH,
[(C₁₁H₂₃O—(CH₂—CH₂O)₄]₂(EtO)Si—CH₂—CH(CH₃)—CH₂—SH,
[(C₁₁H₂₃O—(CH₂—CH₂O)₅]₂(EtO)Si—CH₂—CH(CH₃)—CH₂—SH,
[(C₁₁H₂₃O—(CH₂—CH₂O)₆]₂(EtO)Si—CH₂—CH(CH₃)—CH₂—SH,
[(C₁₂H₂₅O—(CH₂—CH₂O)₂]₂(EtO)Si—CH₂—CH(CH₃)—CH₂—SH,
[(C₁₂H₂₅O—(CH₂—CH₂O)₃]₂(EtO)Si—CH₂—CH(CH₃)—CH₂—SH,
[(C₁₂H₂₅O—(CH₂—CH₂O)₄]₂(EtO)Si—CH₂—CH(CH₃)—CH₂—SH,
[(C₁₂H₂₅O—(CH₂—CH₂O)₅]₂(EtO)Si—CH₂—CH(CH₃)—CH₂—SH,
[(C₁₂H₂₅O—(CH₂—CH₂O)₆]₂(EtO)Si—CH₂—CH(CH₃)—CH₂—SH,
[(C₁₃H₂₇O—(CH₂—CH₂O)₂]₂(EtO)Si—CH₂—CH(CH₃)—CH₂—SH,
[(C₁₃H₂₇O—(CH₂—CH₂O)₃]₂(EtO)Si—CH₂—CH(CH₃)—CH₂—SH,
[(C₁₃H₂₇O—(CH₂—CH₂O)₄]₂(EtO)Si—CH₂—CH(CH₃)—CH₂—SH,
[(C₁₃H₂₇O—(CH₂—CH₂O)₅]₂(EtO)Si—CH₂—CH(CH₃)—CH₂—SH,
[(C₁₃H₂₇O—(CH₂—CH₂O)₆]₂(EtO)Si—CH₂—CH(CH₃)—CH₂—SH,
[(C₁₄H₂₉O—(CH₂—CH₂O)₂]₂(EtO)Si—CH₂—CH(CH₃)—CH₂—SH,
[(C₁₄H₂₉O—(CH₂—CH₂O)₃]₂(EtO)Si—CH₂—CH(CH₃)—CH₂—SH,
[(C₁₄H₂₉O—(CH₂—CH₂O)₄]₂(EtO)Si—CH₂—CH(CH₃)—CH₂—SH,
[(C₁₄H₂₉O—(CH₂—CH₂O)₅]₂(EtO)Si—CH₂—CH(CH₃)—CH₂—SH,
[(C₁₄H₂₉O—(CH₂—CH₂O)₆]₂(EtO)Si—CH₂—CH(CH₃)—CH₂—SH,
[(C₁₅H₃₁O—(CH₂—CH₂O)₂]₂(EtO)Si—CH₂—CH(CH₃)—CH₂—SH,
[(C₁₅H₃₁O—(CH₂—CH₂O)₃]₂(EtO)Si—CH₂—CH(CH₃)—CH₂—SH,
[(C₁₅H₃₁O—(CH₂—CH₂O)₄]₂(EtO)Si—CH₂—CH(CH₃)—CH₂—SH,
[(C₁₅H₃₁O—(CH₂—CH₂O)₅]₂(EtO)Si—CH₂—CH(CH₃)—CH₂—SH,
[(C₁₅H₃₁O—(CH₂—CH₂O)₆]₂(EtO)Si—CH₂—CH(CH₃)—CH₂—SH,
[(C₁₆H₃₃O—(CH₂—CH₂O)₂]₂(EtO)Si—CH₂—CH(CH₃)—CH₂—SH,
[(C₁₆H₃₃O—(CH₂—CH₂O)₃]₂(EtO)Si—CH₂—CH(CH₃)—CH₂—SH,
[(C₁₆H₃₃O—(CH₂—CH₂O)₄]₂(EtO)Si—CH₂—CH(CH₃)—CH₂—SH,
[(C₁₆H₃₃O—(CH₂—CH₂O)₅]₂(EtO)Si—CH₂—CH(CH₃)—CH₂—SH,
[(C₁₆H₃₃O—(CH₂—CH₂O)₆]₂(EtO)Si—CH₂—CH(CH₃)—CH₂—SH,
[(C₁₇H₃₅O—(CH₂—CH₂O)₂]₂(EtO)Si—CH₂—CH(CH₃)—CH₂—SH,
[(C₁₇H₃₅O—(CH₂—CH₂O)₃]₂(EtO)Si—CH₂—CH(CH₃)—CH₂—SH,
[(C₁₇H₃₅O—(CH₂—CH₂O)₄]₂(EtO)Si—CH₂—CH(CH₃)—CH₂—SH,
[(C₁₇H₃₅O—(CH₂—CH₂O)₅]₂(EtO)Si—CH₂—CH(CH₃)—CH₂—SH,
[(C₁₇H₃₅O—(CH₂—CH₂O)₆]₂(EtO)Si—CH₂—CH(CH₃)—CH₂—SH,
[(C₁₁H₂₃O—(CH₂—CH₂O)₂]₃Si—CH₂—CH(CH₃)—CH₂—SH,
[(C₁₁H₂₃O—(CH₂—CH₂O)₃]₃Si—CH₂—CH(CH₃)—CH₂—SH,

[(C₁₁H₂₃O—(CH₂—CH₂O)₄]₃Si—CH₂—CH(CH₃)—CH₂—SH,
[(C₁₁H₂₃O—(CH₂—CH₂O)₅]₃Si—CH₂—CH(CH₃)—CH₂—SH,
[(C₁₁H₂₃O—(CH₂—CH₂O)₆]₃Si—CH₂—CH(CH₃)—CH₂—SH,
[(C₁₂H₂₅O—(CH₂—CH₂O)₂]₃Si—CH₂—CH(CH₃)—CH₂—SH,
[(C₁₂H₂₅O—(CH₂—CH₂O)₃]₃Si—CH₂—CH(CH₃)—CH₂—SH,
[(C₁₂H₂₅O—(CH₂—CH₂O)₄]₃Si—CH₂—CH(CH₃)—CH₂—SH,
[(C₁₂H₂₅O—(CH₂—CH₂O)₅]₃Si—CH₂—CH(CH₃)—CH₂—SH,
[(C₁₂H₂₅O—(CH₂—CH₂O)₆]₃Si—CH₂—CH(CH₃)—CH₂—SH,
[(C₁₃H₂₇O—(CH₂—CH₂O)₂]₃Si—CH₂—CH(CH₃)—CH₂—SH,
[(C₁₃H₂₇O—(CH₂—CH₂O)₃]₃Si—CH₂—CH(CH₃)—CH₂—SH,
[(C₁₃H₂₇O—(CH₂—CH₂O)₄]₃Si—CH₂—CH(CH₃)—CH₂—SH,
[(C₁₃H₂₇O—(CH₂—CH₂O)₅]₃Si—CH₂—CH(CH₃)—CH₂—SH,
[(C₁₃H₂₇O—(CH₂—CH₂O)₆]₃Si—CH₂—CH(CH₃)—CH₂—SH,
[(C₁₄H₂₉O—(CH₂—CH₂O)₂]₃Si—CH₂—CH(CH₃)—CH₂—SH,
[(C₁₄H₂₉O—(CH₂—CH₂O)₃]₃Si—CH₂—CH(CH₃)—CH₂—SH,
[(C₁₄H₂₉O—(CH₂—CH₂O)₄]₃Si—CH₂—CH(CH₃)—CH₂—SH,
[(C₁₄H₂₉O—(CH₂—CH₂O)₅]₃Si—CH₂—CH(CH₃)—CH₂—SH,
[(C₁₄H₂₉O—(CH₂—CH₂O)₆]₃Si—CH₂—CH(CH₃)—CH₂—SH,
[(C₁₅H₃₁O—(CH₂—CH₂O)₂]₃Si—CH₂—CH(CH₃)—CH₂—SH,
[(C₁₅H₃₁O—(CH₂—CH₂O)₃]₃Si—CH₂—CH(CH₃)—CH₂—SH,
[(C₁₅H₃₁O—(CH₂—CH₂O)₄]₃Si—CH₂—CH(CH₃)—CH₂—SH,
[(C₁₅H₃₁O—(CH₂—CH₂O)₅]₃Si—CH₂—CH(CH₃)—CH₂—SH,
[(C₁₅H₃₁O—(CH₂—CH₂O)₆]₃Si—CH₂—CH(CH₃)—CH₂—SH,
[(C₁₆H₃₃O—(CH₂—CH₂O)₂]₃Si—CH₂—CH(CH₃)—CH₂—SH,
[(C₁₆H₃₃O—(CH₂—CH₂O)₃]₃Si—CH₂—CH(CH₃)—CH₂—SH,
[(C₁₆H₃₃O—(CH₂—CH₂O)₄]₃Si—CH₂—CH(CH₃)—CH₂—SH,
[(C₁₆H₃₃O—(CH₂—CH₂O)₅]₃Si—CH₂—CH(CH₃)—CH₂—SH,
[(C₁₆H₃₃O—(CH₂—CH₂O)₆]₃Si—CH₂—CH(CH₃)—CH₂—SH,
[(C₁₇H₃₅O—(CH₂—CH₂O)₂]₃Si—CH₂—CH(CH₃)—CH₂—SH,
[(C₁₇H₃₅O—(CH₂—CH₂O)₃]₃Si—CH₂—CH(CH₃)—CH₂—SH,
[(C₁₇H₃₅O—(CH₂—CH₂O)₄]₃Si—CH₂—CH(CH₃)—CH₂—SH,
[(C₁₇H₃₅O—(CH₂—CH₂O)₅]₃Si—CH₂—CH(CH₃)—CH₂—SH,
[(C₁₇H₃₅O—(CH₂—CH₂O)₆]₃Si—CH₂—CH(CH₃)—CH₂—SH, wherein $R^6$ can be branched or unbranched.

Preferred compounds of the formula I where $R^4$=CN can be:
[(C₁₁H₂₃O—(CH₂—CH₂O)₂](EtO)₂Si(CH₂)₃SCN,
[(C₁₁H₂₃O—(CH₂—CH₂O)₃](EtO)₂Si(CH₂)₃SCN,
[(C₁₁H₂₃O—(CH₂—CH₂O)₄](EtO)₂Si(CH₂)₃SCN,
[(C₁₁H₂₃O—(CH₂—CH₂O)₅](EtO)₂Si(CH₂)₃SCN,
[(C₁₁H₂₃O—(CH₂—CH₂O)₆](EtO)₂Si(CH₂)₃SCN,
[(C₁₂H₂₅O—(CH₂—CH₂O)₂](EtO)₂Si(CH₂)₃SCN,
[(C₁₂H₂₅O—(CH₂—CH₂O)₃](EtO)₂Si(CH₂)₃SCN,
[(C₁₂H₂₅O—(CH₂—CH₂O)₄](EtO)₂Si(CH₂)₃SCN,
[(C₁₂H₂₅O—(CH₂—CH₂O)₅](EtO)₂Si(CH₂)₃SCN,
[(C₁₂H₂₅O—(CH₂—CH₂O)₆](EtO)₂Si(CH₂)₃SCN,
[(C₁₃H₂₇O—(CH₂—CH₂O)₂](EtO)₂Si(CH₂)₃SCN,
[(C₁₃H₂₇O—(CH₂—CH₂O)₃](EtO)₂Si(CH₂)₃SCN,
[(C₁₃H₂₇O—(CH₂—CH₂O)₄](EtO)₂Si(CH₂)₃SCN,
[(C₁₃H₂₇O—(CH₂—CH₂O)₅](EtO)₂Si(CH₂)₃SCN,
[(C₁₃H₂₇O—(CH₂—CH₂O)₆](EtO)₂Si(CH₂)₃SCN,
[(C₁₄H₂₉O—(CH₂—CH₂O)₂](EtO)₂Si(CH₂)₃SCN,
[(C₁₄H₂₉O—(CH₂—CH₂O)₃](EtO)₂Si(CH₂)₃SCN,
[(C₁₄H₂₉O—(CH₂—CH₂O)₄](EtO)₂Si(CH₂)₃SCN,
[(C₁₄H₂₉O—(CH₂—CH₂O)₅](EtO)₂Si(CH₂)₃SCN,
[(C₁₄H₂₉O—(CH₂—CH₂O)₆](EtO)₂Si(CH₂)₃SCN,
[(C₁₁H₂₃O—(CH₂—CH₂O)₂]₂(EtO)Si(CH₂)₃SCN,
[(C₁₁H₂₃O—(CH₂—CH₂O)₃]₂(EtO)Si(CH₂)₃SCN,
[(C₁₁H₂₃O—(CH₂—CH₂O)₄]₂(EtO)Si(CH₂)₃SCN,
[(C₁₁H₂₃O—(CH₂—CH₂O)₅]₂(EtO)Si(CH₂)₃SCN,
[(C₁₁H₂₃O—(CH₂—CH₂O)₆]₂(EtO)Si(CH₂)₃SCN,
[(C₁₂H₂₅O—(CH₂—CH₂O)₂]₂(EtO)Si(CH₂)₃SCN,
[(C₁₂H₂₅O—(CH₂—CH₂O)₃]₂(EtO)Si(CH₂)₃SCN,
[(C₁₂H₂₅O—(CH₂—CH₂O)₄]₂(EtO)Si(CH₂)₃SCN,
[(C₁₂H₂₅O—(CH₂—CH₂O)₅]₂(EtO)Si(CH₂)₃SCN,
[(C₁₂H₂₅O—(CH₂—CH₂O)₆]₂(EtO)Si(CH₂)₃SCN,
[(C₁₃H₂₇O—(CH₂—CH₂O)₂]₂(EtO)Si(CH₂)₃SCN,
[(C₁₃H₂₇O—(CH₂—CH₂O)₃]₂(EtO)Si(CH₂)₃SCN,
[(C₁₃H₂₇O—(CH₂—CH₂O)₄]₂(EtO)Si(CH₂)₃SCN,
[(C₁₃H₂₇O—(CH₂—CH₂O)₅]₂(EtO)Si(CH₂)₃SCN,
[(C₁₃H₂₇O—(CH₂—CH₂O)₆]₂(EtO)Si(CH₂)₃SCN,
[(C₁₄H₂₉O—(CH₂—CH₂O)₂]₂(EtO)Si(CH₂)₃SCN,
[(C₁₄H₂₉O—(CH₂—CH₂O)₃]₂(EtO)Si(CH₂)₃SCN,
[(C₁₄H₂₉O—(CH₂—CH₂O)₄]₂(EtO)Si(CH₂)₃SCN,
[(C₁₄H₂₉O—(CH₂—CH₂O)₅]₂(EtO)Si(CH₂)₃SCN,
[(C₁₄H₂₉O—(CH₂—CH₂O)₆]₂(EtO)Si(CH₂)₃SCN,
[(C₁₁H₂₃O—(CH₂—CH₂O)₂]₃Si(CH₂)₃SCN,
[(C₁₁H₂₃O—(CH₂—CH₂O)₃]₃Si(CH₂)₃SCN,
[(C₁₁H₂₃O—(CH₂—CH₂O)₄]₃Si(CH₂)₃SCN,
[(C₁₁H₂₃O—(CH₂—CH₂O)₅]₃Si(CH₂)₃SCN,
[(C₁₁H₂₃O—(CH₂—CH₂O)₆]₃Si(CH₂)₃SCN,
[(C₁₂H₂₅O—(CH₂—CH₂O)₂]₃Si(CH₂)₃SCN,
[(C₁₂H₂₅O—(CH₂—CH₂O)₃]₃Si(CH₂)₃SCN,
[(C₁₂H₂₅O—(CH₂—CH₂O)₄]₃Si(CH₂)₃SCN,
[(C₁₂H₂₅O—(CH₂—CH₂O)₅]₃Si(CH₂)₃SCN,
[(C₁₂H₂₅O—(CH₂—CH₂O)₆]₃Si(CH₂)₃SCN,
[(C₁₃H₂₇O—(CH₂—CH₂O)₂]₃Si(CH₂)₃SCN,
[(C₁₃H₂₇O—(CH₂—CH₂O)₃]₃Si(CH₂)₃SCN,
[(C₁₃H₂₇O—(CH₂—CH₂O)₄]₃Si(CH₂)₃SCN,
[(C₁₃H₂₇O—(CH₂—CH₂O)₅]₃Si(CH₂)₃SCN,
[(C₁₃H₂₇O—(CH₂—CH₂O)₆]₃Si(CH₂)₃SCN,
[(C₁₄H₂₉O—(CH₂—CH₂O)₂]₃Si(CH₂)₃SCN,
[(C₁₄H₂₉O—(CH₂—CH₂O)₃]₃Si(CH₂)₃SCN,
[(C₁₄H₂₉O—(CH₂—CH₂O)₄]₃Si(CH₂)₃SCN,
[(C₁₄H₂₉O—(CH₂—CH₂O)₅]₃Si(CH₂)₃SCN or
[(C₁₄H₂₉O—(CH₂—CH₂O)₆]₃Si(CH₂)₃SCN, wherein $R^6$ can be branched or unbranched.

Preferred compounds of the formula I where $R^4$=—C(=O)—$R^9$ and $R^9$=branched or unbranched —C₅H₁₁, —C₆H₁₃, —C₇H₁₅, —C₈H₁₇, —C₉H₁₉, —C₁₀H₂₁, —$C_{11}H_{23}$, —$C_{12}H_{25}$, —$C_{13}H_{27}$, —$C_{14}H_{29}$, —$C_{15}H_{31}$, —$C_{16}H_{33}$, —$C_{17}H_{35}$ and —$C_6H_5$ (phenyl) can be:

[($C_{11}H_{23}$O—($CH_2$—$CH_2$O)$_2$](EtO)$_2$Si($CH_2$)$_3$—C(=O)—$R^9$,
[($C_{11}H_{23}$O—($CH_2$—$CH_2$O)$_3$](EtO)$_2$Si($CH_2$)$_3$—C(=O)—$R^9$,
[($C_{11}H_{23}$O—($CH_2$—$CH_2$O)$_4$](EtO)$_2$Si($CH_2$)$_3$—C(=O)—$R^9$,
[($C_{11}H_{23}$O—($CH_2$—$CH_2$O)$_5$](EtO)$_2$Si($CH_2$)$_3$—C(=O)—$R^9$,
[($C_{11}H_{23}$O—($CH_2$—$CH_2$O)$_6$](EtO)$_2$Si($CH_2$)$_3$—C(=O)—$R^9$,
[($C_{12}H_{25}$O—($CH_2$—$CH_2$O)$_2$](EtO)$_2$Si($CH_2$)$_3$—C(=O)—$R^9$,
[($C_{12}H_{25}$O—($CH_2$—$CH_2$O)$_3$](EtO)$_2$Si($CH_2$)$_3$—C(=O)—$R^9$,
[($C_{12}H_{25}$O—($CH_2$—$CH_2$O)$_4$](EtO)$_2$Si($CH_2$)$_3$—C(=O)—$R^9$,
[($C_{12}H_{25}$O—($CH_2$—$CH_2$O)$_5$](EtO)$_2$Si($CH_2$)$_3$—C(=O)—$R^9$,
[($C_{12}H_{25}$O—($CH_2$—$CH_2$O)$_6$](EtO)$_2$Si($CH_2$)$_3$—C(=O)—$R^9$,
[($C_{13}H_{27}$O—($CH_2$—$CH_2$O)$_2$](EtO)$_2$Si($CH_2$)$_3$—C(=O)—$R^9$,
[($C_{13}H_{27}$O—($CH_2$—$CH_2$O)$_3$](EtO)$_2$Si($CH_2$)$_3$—C(=O)—$R^9$,
[($C_{13}H_{27}$O—($CH_2$—$CH_2$O)$_4$](EtO)$_2$Si($CH_2$)$_3$—C(=O)—$R^9$,
[($C_{13}H_{27}$O—($CH_2$—$CH_2$O)$_5$](EtO)$_2$Si($CH_2$)$_3$—C(=O)—$R^9$,
[($C_{13}H_{27}$O—($CH_2$—$CH_2$O)$_6$](EtO)$_2$Si($CH_2$)$_3$—C(=O)—$R^9$,
[($C_{14}H_{29}$O—($CH_2$—$CH_2$O)$_2$](EtO)$_2$Si($CH_2$)$_3$—C(=O)—$R^9$,
[($C_{14}H_{29}$O—($CH_2$—$CH_2$O)$_3$](EtO)$_2$Si($CH_2$)$_3$—C(=O)—$R^9$,
[($C_{14}H_{29}$O—($CH_2$—$CH_2$O)$_4$](EtO)$_2$Si($CH_2$)$_3$—C(=O)—$R^9$,
[($C_{14}H_{29}$O—($CH_2$—$CH_2$O)$_5$](EtO)$_2$Si($CH_2$)$_3$—C(=O)—$R^9$,
[($C_{14}H_{29}$O—($CH_2$—$CH_2$O)$_6$](EtO)$_2$Si($CH_2$)$_3$—C(=O)—$R^9$,
[($C_{11}H_{23}$O—($CH_2$—$CH_2$O)$_2$]$_2$(EtO)Si($CH_2$)$_3$—C(=O)—$R^9$,
[($C_{11}H_{23}$O—($CH_2$—$CH_2$O)$_3$]$_2$(EtO)Si($CH_2$)$_3$—C(=O)—$R^9$,
[($C_{11}H_{23}$O—($CH_2$—$CH_2$O)$_4$]$_2$(EtO)Si($CH_2$)$_3$—C(=O)—$R^9$,
[($C_{11}H_{23}$O—($CH_2$—$CH_2$O)$_5$]$_2$(EtO)Si($CH_2$)$_3$—C(=O)—$R^9$,
[($C_{11}H_{23}$O—($CH_2$—$CH_2$O)$_6$]$_2$(EtO)Si($CH_2$)$_3$—C(=O)—$R^9$,
[($C_{12}H_{25}$O—($CH_2$—$CH_2$O)$_2$]$_2$(EtO)Si($CH_2$)$_3$—C(=O)—$R^9$,
[($C_{12}H_{25}$O—($CH_2$—$CH_2$O)$_3$]$_2$(EtO)Si($CH_2$)$_3$—C(=O)—$R^9$,
[($C_{12}H_{25}$O—($CH_2$—$CH_2$O)$_4$]$_2$(EtO)Si($CH_2$)$_3$—C(=O)—$R^9$,
[($C_{12}H_{25}$O—($CH_2$—$CH_2$O)$_5$]$_2$(EtO)Si($CH_2$)$_3$—C(=O)—$R^9$,
[($C_{12}H_{25}$O—($CH_2$—$CH_2$O)$_6$]$_2$(EtO)Si($CH_2$)$_3$—C(=O)—$R^9$,
[($C_{13}H_{27}$O—($CH_2$—$CH_2$O)$_2$]$_2$(EtO)Si($CH_2$)$_3$—C(=O)—$R^9$,
[($C_{13}H_{27}$O—($CH_2$—$CH_2$O)$_3$]$_2$(EtO)Si($CH_2$)$_3$—C(=O)—$R^9$,
[($C_{13}H_{27}$O—($CH_2$—$CH_2$O)$_4$]$_2$(EtO)Si($CH_2$)$_3$—C(=O)—$R^9$,
[($C_{13}H_{27}$O—($CH_2$—$CH_2$O)$_5$]$_2$(EtO)Si($CH_2$)$_3$—C(=O)—$R^9$,
[($C_{13}H_{27}$O—($CH_2$—$CH_2$O)$_6$]$_2$(EtO)Si($CH_2$)$_3$—C(=O)—$R^9$,
[($C_{14}H_{29}$O—($CH_2$—$CH_2$O)$_2$]$_2$(EtO)Si($CH_2$)$_3$—C(=O)—$R^9$,
[($C_{14}H_{29}$O—($CH_2$—$CH_2$O)$_3$]$_2$(EtO)Si($CH_2$)$_3$—C(=O)—$R^9$,
[($C_{14}H_{29}$O—($CH_2$—$CH_2$O)$_4$]$_2$(EtO)Si($CH_2$)$_3$—C(=O)—$R^9$,
[($C_{14}H_{29}$O—($CH_2$—$CH_2$O)$_5$]$_2$(EtO)Si($CH_2$)$_3$—C(=O)—$R^9$,
[($C_{14}H_{29}$O—($CH_2$—$CH_2$O)$_6$]$_2$(EtO)Si($CH_2$)$_3$—C(=O)—$R^9$,
[($C_{11}H_{23}$O—($CH_2$—$CH_2$O)$_2$]$_3$Si($CH_2$)$_3$—C(=O)—$R^9$,
[($C_{11}H_{23}$O—($CH_2$—$CH_2$O)$_3$]$_3$Si($CH_2$)$_3$—C(=O)—$R^9$,
[($C_{11}H_{23}$O—($CH_2$—$CH_2$O)$_4$]$_3$Si($CH_2$)$_3$—C(=O)—$R^9$,
[($C_{11}H_{23}$O—($CH_2$—$CH_2$O)$_5$]$_3$Si($CH_2$)$_3$—C(=O)—$R^9$,
[($C_{11}H_{23}$O—($CH_2$—$CH_2$O)$_6$]$_3$Si($CH_2$)$_3$—C(=O)—$R^9$,
[($C_{12}H_{25}$O—($CH_2$—$CH_2$O)$_2$]$_3$Si($CH_2$)$_3$—C(=O)—$R^9$,
[($C_{12}H_{25}$O—($CH_2$—$CH_2$O)$_3$]$_3$Si($CH_2$)$_3$—C(=O)—$R^9$,
[($C_{12}H_{25}$O—($CH_2$—$CH_2$O)$_4$]$_3$Si($CH_2$)$_3$—C(=O)—$R^9$,
[($C_{12}H_{25}$O—($CH_2$—$CH_2$O)$_5$]$_3$Si($CH_2$)$_3$—C(=O)—$R^9$,
[($C_{12}H_{25}$O—($CH_2$—$CH_2$O)$_6$]$_3$Si($CH_2$)$_3$—C(=O)—$R^9$,
[($C_{13}H_{27}$O—($CH_2$—$CH_2$O)$_2$]$_3$Si($CH_2$)$_3$—C(=O)—$R^9$,
[($C_{13}H_{27}$O—($CH_2$—$CH_2$O)$_3$]$_3$Si($CH_2$)$_3$—C(=O)—$R^9$,
[($C_{13}H_{27}$O—($CH_2$—$CH_2$O)$_4$]$_3$Si($CH_2$)$_3$—C(=O)—$R^9$,
[($C_{13}H_{27}$O—($CH_2$—$CH_2$O)$_5$]$_3$Si($CH_2$)$_3$—C(=O)—$R^9$,
[($C_{13}H_{27}$O—($CH_2$—$CH_2$O)$_6$]$_3$Si($CH_2$)$_3$—C(=O)—$R^9$,
[($C_{14}H_{29}$O—($CH_2$—$CH_2$O)$_2$]$_3$Si($CH_2$)$_3$—C(=O)—$R^9$,
[($C_{14}H_{29}$O—($CH_2$—$CH_2$O)$_3$]$_3$Si($CH_2$)$_3$—C(=O)—$R^9$,
[($C_{14}H_{29}$O—($CH_2$—$CH_2$O)$_4$]$_3$Si($CH_2$)$_3$—C(=O)—$R^9$,
[($C_{14}H_{29}$O—($CH_2$—$CH_2$O)$_5$]$_3$Si($CH_2$)$_3$—C(=O)—$R^9$, or
[($C_{14}H_{29}$O—($CH_2$—$CH_2$O)$_6$]$_3$Si($CH_2$)$_3$—C(=O)—$R^9$, $R^6$ can preferably be $C_{12}$ to $C_{17}$, very particularly preferably $C_{12}$ to $C_{16}$, exceptionally preferably $C_{12}$ to $C_{14}$, unsubstituted or substituted, branched or unbranched monovalent alkyl.

$R^6$ can be a —$C_{11}H_{23}$, —$C_{12}H_{25}$, —$C_{13}H_{27}$, —$C_{14}H_{29}$, —$C_{15}H_{31}$, —$C_{16}H_{33}$ or —$C_{17}H_{35}$ alkyl group.

$R^6$ can preferably be $C_{11}$ to $C_{35}$, particularly preferably $C_{11}$ to $C_{30}$, very particularly preferably $C_{12}$ to $C_{30}$, exceptionally preferably $C_{13}$ to $C_{20}$, unsubstituted or substituted, branched or unbranched monovalent alkyl.

$R^6$ can preferably be $C_{11}$ to $C_{14}$ and/or $C_{16}$ to $C_{30}$, very particularly preferably $C_{11}$ to $C_{14}$ and/or $C_{16}$ to $C_{25}$, exceptionally preferably $C_{12}$ to $C_{14}$ and/or $C_{16}$ to $C_{20}$, unsubstituted or substituted, branched or unbranched monovalent aralkyl.

$R^6$ as alkenyl can be $C_{11}H_{21}$, —$C_{12}H_{23}$, —$C_{13}H_{25}$, —$C_{14}H_{27}$, —$C_{15}H_{29}$, —$C_{16}H_{31}$ or —$C_{17}H_{33}$.

$R^1$ can be an alkoxylated castor oil (e.g. CAS 61791-12-6).

$R^1$ can be an alkoxylated oleylamine (e.g. CAS 26635-93-8).

The polyether group $(R^5O)_m$ can contain random ethylene oxide and propylene oxide units or polyether blocks of polyethylene oxide and polypropylene oxide.

The polyether group can have a molecular weight distribution.

The mercaptosilane of the general formula I can be a mixture of various mercaptosilanes of the general formula I wherein $R^6$ comprises different C atom chain lengths and has a molecular weight distribution.

The silane of the general formula I where $R^4$ is —CN can be a mixture of various silanes of the general formula I where $R^4$ is —CN or of condensation products thereof or of silanes of the general formula I where $R^4$ is —CN and of condensation products thereof.

The silane of the general formula I where $R^4$ is (C=O)—$R^9$ can be a mixture of various silanes of the general formula I where $R^4$ is (C=O)—$R^9$ or of condensation products thereof or of silanes of the general formula I where $R^4$ is (C=O)—$R^9$ and of condensation products thereof.

The polyether group $(R^5—O)_m$ can preferably be:
(—O—CH$_2$—CH$_2$—)$_a$,
(—O—CH(CH$_3$)—CH$_2$—)$_a$,
(—O—CH$_2$—CH(CH$_3$)—)$_a$,
(—O—CH$_2$—CH$_2$—)$_a$(—O—CH(CH$_3$)—CH$_2$—),
(—O—CH$_2$—CH$_2$—)(—O—CH(CH$_3$)—CH$_2$—)$_a$,
(—O—CH$_2$—CH$_2$—)$_a$(—O—CH$_2$—CH(CH$_3$)—),
(—O—CH$_2$—CH$_2$—)(—O—CH$_2$—CH(CH$_3$)—)$_a$,
(—O—CH(CH$_3$)—CH$_2$—)$_a$(—O—CH$_2$—CH(CH$_3$)—),
(—O—CH(CH$_3$)—CH$_2$—)(—O—CH$_2$—CH(CH$_3$)—)$_a$,
(—O—CH$_2$—CH$_2$—)$_a$(—O—CH(CH$_3$)—CH$_2$—)$_b$(—O—CH$_2$—CH(CH$_3$)—)$_c$ or a combination with one another, wherein a, b and c are independent of one another and a is 1-50, preferably 2-30, particularly preferably 3-20, very particularly preferably 4-15, exceptionally preferably 5-12, b is 1-50, preferably 2-30, particularly preferably 3-20, very particularly preferably 4-15, exceptionally preferably 5-12 and
c is 1-50, preferably 2-30, particularly preferably 3-20, very particularly preferably 4-15, exceptionally preferably 5-12.

The indices a, b and c are integers and designate the number of recurring units.

For $R^4$ as —H, —CN or —C(=O)—$R^9$, the group $(R^5—O)_m$ can preferably contain ethylene oxide (CH$_2$—CH$_2$—O)$_a$ or propylene oxide (CH(CH$_3$)—CH$_2$—O)$_a$ or (CH$_2$—CH(CH$_3$)—O)$_a$ units.

For $R^4$ as —H, —CN or —C(=O)—$R^9$, the group $(R^5—O)_m$ can preferably contain ethylene oxide (CH$_2$—CH$_2$—O)$_a$ and propylene oxide (CH(CH$_3$)—CH$_2$—O)$_a$ or (CH$_2$—CH(CH$_3$)—O)$_a$ units in random distribution or in blocks.

For $R^4$ as —H, the alkyl polyether group $(R^5—O)_m$ can preferably contain ethylene oxide (CH$_2$—CH$_2$—O)$_a$ and propylene oxide (CH(CH$_3$)—CH$_2$—O)$_a$ or (CH$_2$—CH(CH$_3$)—O)$_a$ units in random distribution or in blocks.

For $R^4$ as —H, the group $(R^5—O)_m$ can preferably contain propylene oxide (CH(CH$_3$)—CH$_2$—O)$_a$ or (CH$_2$—CH(CH$_3$)—O)$_a$ units.

For $R^4$ as —H, —CN or —C(=O)—$R^9$, the alkyl polyether group O—$(R^5—O)_m$—$R^6$ can be:
O—(CH$_2$—CH$_2$O)$_2$—C$_{11}$H$_{23}$, O—(CH$_2$—CH$_2$O)$_3$—C$_{11}$H$_{23}$, O—(CH$_2$—CH$_2$O)$_4$—C$_{11}$H$_{23}$, O—(CH$_2$—CH$_2$O)$_5$—C$_{11}$H$_{23}$, O—(CH$_2$—CH$_2$O)$_6$—C$_{11}$H$_{23}$, O—(CH$_2$—CH$_2$O)$_7$—C$_{11}$H$_{23}$,
O—(CH(CH$_3$)—CH$_2$O)$_2$—C$_{11}$H$_{23}$, O—(CH(CH$_3$)—CH$_2$O)$_3$—C$_{11}$H$_{23}$, O—(CH(CH$_3$)—CH$_2$O)$_4$—C$_{11}$H$_{23}$, O—(CH(CH$_3$)—CH$_2$O)$_5$—C$_{11}$H$_{23}$, O—(CH(CH$_3$)—CH$_2$O)$_6$—C$_{11}$H$_{23}$, O—(CH(CH$_3$)—CH$_2$O)$_7$—C$_{11}$H$_{23}$,
O—(CH$_2$—CH$_2$O)$_2$—C$_{12}$H$_{25}$, O—(CH$_2$—CH$_2$O)$_3$—C$_{12}$H$_{25}$, O—(CH$_2$—CH$_2$O)$_4$—C$_{12}$H$_{25}$, O—(CH$_2$—CH$_2$O)$_5$—C$_{12}$H$_{25}$, O—(CH$_2$—CH$_2$O)$_6$—C$_{12}$H$_{25}$, O—(CH$_2$—CH$_2$O)$_7$—C$_{12}$H$_{25}$,
O—(CH(CH$_3$)—CH$_2$O)$_2$—C$_{12}$H$_{25}$, O—(CH(CH$_3$)—CH$_2$O)$_3$—C$_{12}$H$_{25}$, O—(CH(CH$_3$)—CH$_2$O)$_4$—C$_{12}$H$_{25}$, O—(CH(CH$_3$)—CH$_2$O)$_5$—C$_{12}$H$_{25}$, O—(CH(CH$_3$)—CH$_2$O)$_6$—C$_{12}$H$_{25}$, O—(CH(CH$_3$)—CH$_2$O)$_7$—C$_{12}$H$_{25}$,
O—(CH$_2$—CH$_2$O)$_2$—C$_{13}$H$_{27}$, O—(CH$_2$—CH$_2$O)$_3$—C$_{13}$H$_{27}$, O—(CH$_2$—CH$_2$O)$_4$—C$_{13}$H$_{27}$, O—(CH$_2$—CH$_2$O)$_5$—C$_{13}$H$_{27}$, O—(CH$_2$—CH$_2$O)$_6$—C$_{13}$H$_{27}$, O—(CH$_2$—CH$_2$O)$_7$—C$_{13}$H$_{27}$,
O—(CH(CH$_3$)—CH$_2$O)$_2$—C$_{13}$H$_{27}$, O—(CH(CH$_3$)—CH$_2$O)$_3$—C$_{13}$H$_{27}$, O—(CH(CH$_3$)—CH$_2$O)$_4$—C$_{13}$H$_{27}$, O—(CH(CH$_3$)—CH$_2$O)$_5$—C$_{13}$H$_{27}$, O—(CH(CH$_3$)—CH$_2$O)$_6$—CH$_3$H$_{27}$O—(CH(CH$_3$)—CH$_2$O)$_7$—C$_{13}$H$_{27}$,
O—(CH$_2$—CH$_2$O)$_2$—C$_{14}$H$_{29}$, O—(CH$_2$—CH$_2$O)$_3$—C$_{14}$H$_{29}$, O—(CH$_2$—CH$_2$O)$_4$—C$_{14}$H$_{29}$, O—(CH$_2$—CH$_2$O)$_5$—C$_{14}$H$_{29}$, O—(CH$_2$—CH$_2$O)$_6$—C$_{14}$H$_{29}$, O—(CH$_2$—CH$_2$O)$_7$—C$_{14}$H$_{29}$,
O—(CH(CH$_3$)—CH$_2$O)$_2$—C$_{14}$H$_{29}$, O—(CH(CH$_3$)—CH$_2$O)$_3$—C$_{14}$H$_{29}$, O—(CH(CH$_3$)—CH$_2$O)$_4$—C$_{14}$H$_{29}$, O—(CH(CH$_3$)—CH$_2$O)$_5$—C$_{14}$H$_{29}$, O—(CH(CH$_3$)—CH$_2$O)$_6$—C$_{14}$H$_{29}$CH$_3$O)$_6$—C$_{14}$H$_{29}$, O—(CH(CH$_3$)—CH$_2$O)$_7$—C$_{14}$H$_{29}$,
O—(CH$_2$—CH$_2$O)$_2$—C$_{15}$H$_{31}$, O—(CH$_2$—CH$_2$O)$_3$—C$_{16}$H$_{31}$, O—(CH$_2$—CH$_2$O)$_4$—C$_{15}$H$_{31}$, O—(CH$_2$—CH$_2$O)$_5$—C$_{15}$H$_{31}$, O—(CH$_2$—CH$_2$O)$_6$—C$_{16}$H$_{31}$, O—(CH$_2$—CH$_2$O)$_7$—C$_{15}$H$_{31}$,
O—(CH(CH$_3$)—CH$_2$O)$_2$—C$_{15}$H$_{31}$, O—(CH(CH$_3$)—CH$_2$O)$_3$—C$_{15}$H$_{31}$, O—(CH(CH$_3$)—CH$_2$O)$_4$—C$_{15}$H$_{31}$, O—(CH(CH$_3$)—CH$_2$O)$_5$—C$_{15}$H$_{31}$, O—(CH(CH$_3$)—CH$_2$O)$_6$—C$_{15}$H$_{31}$, O—(CH(CH$_3$)—CH$_2$O)$_7$—C$_{15}$H$_{31}$,
O—(OH$_2$—CH$_2$O)$_2$—C$_{16}$H$_{33}$, O—(CH$_2$—CH$_2$O)$_3$—C$_{16}$H$_{33}$, O—(CH$_2$—CH$_2$O)$_4$—C$_{16}$H$_{33}$, O—(CH$_2$—CH$_2$O)$_5$—C$_{16}$H$_{33}$, O—(CH$_2$—CH$_2$O)$_6$—C$_{16}$H$_{33}$, O—(CH$_2$—CH$_2$O)$_7$—C$_{16}$H$_{33}$,
O—(CH(CH$_3$)—CH$_2$O)$_2$—C$_{16}$H$_{33}$, O—(CH(CH$_3$)—CH$_2$O)$_3$—C$_{16}$H$_{33}$, O—(CH(CH$_3$)—CH$_2$O)$_4$—C$_{16}$H$_{33}$, O—(CH(CH$_3$)—CH$_2$O)$_5$—C$_{16}$H$_{33$, O—(CH(CH$_3$)—CH$_2$O)$_6$—C$_{16}$H$_{33}$, O—(CH(CH$_3$)—CH$_2$O)$_7$—C$_{16}$H$_{33}$,
O—(CH$_2$—CH$_2$O)$_2$—C$_{17}$H$_{35}$, O—(CH$_2$—CH$_2$O)$_3$—C$_{17}$H$_{35}$, O—(CH$_2$—CH$_2$O)$_4$—C$_{17}$H$_{35}$, O—(CH$_2$—CH$_2$O)$_5$—C$_{17}$H$_{35}$, O—(CH$_2$—CH$_2$O)$_6$—C$_{17}$H$_{35}$, O—(CH$_2$—CH$_2$O)$_7$—C$_{17}$H$_{35}$,
O—(CH(CH$_3$)—CH$_2$O)$_2$—C$_{17}$H$_{35}$, O—(CH(CH$_3$)—CH$_2$O)$_3$—C$_{17}$H$_{35}$, O—(CH(CH$_3$)—CH$_2$O)$_4$—C$_{17}$H$_{35}$, O—(CH(CH$_3$)—CH$_2$O)$_5$—C$_{17}$H$_{35}$, O—(CH(CH$_3$)—CH$_2$O)$_6$—C$_{17}$H$_{35}$ or O—(CH(CH$_3$)—CH$_2$O)$_7$—C$_{17}$H$_{35}$.

The group $R^5$ can be substituted. The group $R^6$ can be $C_{13}H_{27}$.

$R^1$ can be —O—(C$_2$H$_4$—O)$_5$—C$_{11}$H$_{23}$, —O—(C$_2$H$_4$—O)$_5$—C$_{12}$H$_{25}$, —O—(C$_2$H$_4$—O)$_5$—C$_{13}$H$_{27}$, —O—(C$_2$H$_4$—O)$_5$—C$_{14}$H$_{29}$, —O—(C$_2$H$_4$—O)$_5$—C$_{15}$H$_{31}$, —O—(C$_2$H$_4$—O)$_3$—C$_{13}$H$_{27}$, —O—(C$_2$H$_4$—O)$_4$—C$_{13}$H$_{27}$, —O—(C$_2$H$_4$—O)$_6$—C$_{13}$H$_{27}$, —O—(C$_2$H$_4$—O)$_7$—C$_{13}$H$_{27}$, —O—(CH$_2$CH$_2$—O)$_5$—(CH$_2$)$_{10}$CH$_3$, —O—(CH$_2$CH$_2$—O)$_5$—(CH$_2$)$_{11}$CH$_3$, —O—(CH$_2$CH$_2$—O)$_5$—(CH$_2$)$_{12}$CH$_3$, —O—(CH$_2$CH$_2$—O)$_5$—(CH$_2$)$_{13}$CH$_3$, —O—(CH$_2$CH$_2$—O)$_5$—(CH$_2$)$_{14}$CH$_3$, —O—(CH$_2$CH$_2$—O)$_3$—(CH$_2$)$_{12}$CH$_3$, —O—(CH$_2$CH$_2$—O)$_4$—(CH$_2$)$_{12}$CH$_3$, —O—(CH$_2$CH$_2$—O)$_6$—(CH$_2$)$_{12}$CH$_3$, —O—(CH$_2$CH$_2$—O)$_7$—(CH$_2$)$_{12}$CH$_3$,

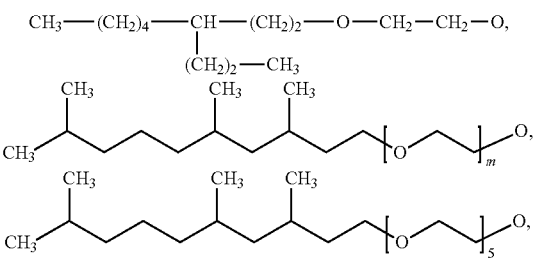

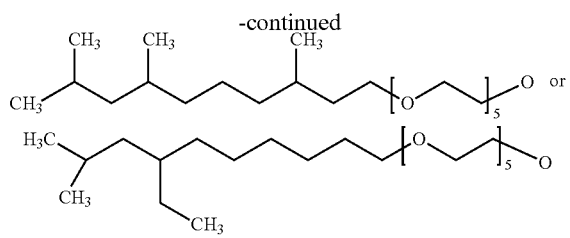

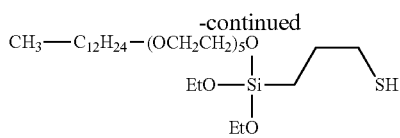

The average branching number of the carbon chain $R^6$ can be 1 to 5, preferably 1.2 to 4. The average branching number is defined in this context as the number of $CH_3$-1 groups.

$R^3$ can denote $CH_2$, $CH_2CH_2$, $CH_2CH_2CH_2$, $CH_2CH_2CH_2CH_2$, $CH(CH_3)$, $CH_2CH(CH_3)$, $CH(CH_3)CH_2$, $C(CH_3)_2$, $CH(C_2H_5)$, $CH_2CH_2CH(CH_3)$, $CH_2CH(CH_3)CH_2$ or

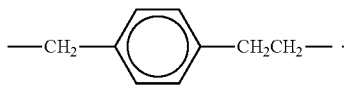

The mercaptosilane of the general formula I can be a mixture of mercaptosilanes of the general formula I in which $R^1$ and $R^2$ are a mixture of alkoxy and alkyl polyether groups.

The mercaptosilane of the general formula I can be a mixture of mercaptosilanes of the general formula I, where $R^2$ is identical or different and is an alkoxy or alkyl polyether group ($R^1$), wherein $R^2$ is different in the mixture.

The mercaptosilane of the general formula I can be a mixture of mercaptosilanes of the general formula I in which $R^1$ and $R^2$ are a mixture of ethoxy and alkyl polyether groups and the alkyl polyether groups from an $R^6$ having an alkyl chain length of 13 C atoms, $R^5$ is ethylene and m is on average 5.

The mercaptosilane of the general formula I can be a mixture of mercaptosilanes of the general formula I, where $R^2$ is identical or different and is an ethoxy or alkylpolyether group ($R^1$), wherein the alkyl polyether group —O—($R^5$—O)$_m$—$R^6$ consists of $R^6$ with an alkyl chain length of 13 C-atoms, $R^5$ is ethylene and m is on average 5, wherein $R^2$ is different in the mixture.

The mercaptosilane of the general formula I can be a mixture of mercaptosilanes of the general formula I in which $R^1$ and $R^2$ are a mixture of alkoxy and alkyl polyether groups and $R^6$ comprises various C atom chain lengths and has a molecular weight distribution.

The mercaptosilane of the general formula I can be a mixture of mercaptosilanes of the general formula I, where $R^2$ is identical or different and is an alkoxy or alkylpolyether group ($R^1$), wherein $R^2$, is different in the mixture, $R^6$ consists of different C-atom chain lengths and has a molecular weight distribution.

The mercaptosilane of the general formula I can preferably be a mixture of mercaptosilanes of the general formula I and can contain

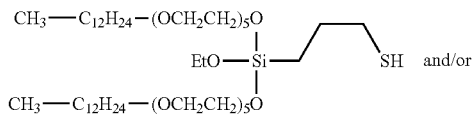 and/or and/or hydrolysis and/or condensation products of the abovementioned compounds.

Condensation products, that is to say oligo- and polysiloxanes, can easily be formed from the silanes of the formula I according to the invention by addition of water and optionally addition of additives.

These oligomeric or polymeric siloxanes of the compounds of the formula I can be used coupling reagents for the same uses as the monomeric compounds of the formula I.

The mercaptosilane compounds according to the invention can also be in the form of a mixture of the oligomeric or polymeric siloxanes of mercaptosilanes of the general formula I or in the form of mixtures of mercaptosilanes of the general formula I with mixtures of the oligomeric or polymeric siloxanes of mercaptosilanes of the general formula I.

The invention also provides a process for the preparation of the mercaptosilanes according to the invention, which is characterized in that silanes of the general formula II

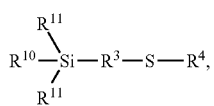

wherein $R^{10}$ is an $R^7O$ group and $R^7$ has the abovementioned meaning, $R^{11}$ is identical or different and is an $R^1$ or C1-C12-alkyl group, $R^3$ and $R^4$ have the abovementioned meaning, are subjected to a catalysed reaction with an alkoxylated alcohol $R^1$—H, wherein $R^1$ has the abovementioned meaning, $R^7$—OH being split off, and $R^7$—OH is separated off from the reaction mixture continuously or discontinuously.

The alkoxylated alcohol $R^1$—OH can be an ethoxylated alcohol.

The molar ratio of the alkoxylated alcohol $R^1$—H to the silane of the general formula II can be at least 0.5, preferably at least 1.0.

Condensation products, that is to say oligo- and polysiloxanes, can easily be formed from the silanes of the formula I according to the invention by addition of water and optionally addition of additives. However, the oligo- and polysiloxanes can also be obtained by oligomerization or co-oligomerization of the corresponding alkoxysilane compounds of the general formula II by addition of water, and by addition of additives and procedures known to the person skilled in the art in this field.

The mercaptosilanes according to the invention can be analysed by means of high-resolution 1-H, 29-Si or 13-C NMR or GPC, and the composition of the substance mixtures formed with respect to the relative distribution of the alkoxy substituents to one another can also be determined.

The mixture of homologous alkoxysilane compounds which is formed can be used as such or also after separation into individual compounds or isolated fractions.

The alkoxylated alcohols $R^1$—H used for the transesterification can be employed both as mixtures of various alcohols and as pure substance. Alkoxylated alcohols $R^1$—H which can be employed are, for example, branched or linear alcohols which are ethoxylated/propoxylated or contain ethylene oxide units and propylene oxide units.

The compounds used as catalysts for the transesterification can be metal-containing or metal-free.

Metal-free compounds which can be employed are organic acids, such as, for example, trifluoroacetic acid, trifluoromethanesulfonic acid or p-toluenesulfonic acid, trialkylammonium compounds $E_3NH^+Z^-$ or bases, such as, for example, trialkylamines $NE_3$, where E=alkyl and $Z^-$=a counter-ion.

The metal compounds employed as catalysts for the transesterification can be transition metal compounds.

Metal compounds which can be employed for the catalysts are metal chlorides, metal oxides, metal oxychlorides, metal sulfides, metal sulfochlorides, metal alcoholates, metal thiolates, metal oxyalcoholates, metal amides, metal imides or transition metal compounds with multiple bonded ligands.

For example, metal compounds which can be used are halides, amides or alcoholates of main group 3 ($M^{3+}$=B, Al, Ga, In, Tl): $M^{3+}(OMe)_3$, $M^{3+}(OEt)_3$, $M^{3+}(OC_3H_7)_3$, $M^{3+}(OC_4H_9)_3$), halides, oxides, sulfides, imides, alcoholates, amides, thiolates and combinations of the substituent classes mentioned with multiple bonded ligands on compounds of the lanthanide group (rare earths, atomic number 58 to 71 in the periodic table of the elements), halides, oxides, sulfides, imides, alcoholates, amides, thiolates and combinations of the substituent classes mentioned with multiple bonded ligands on compounds of sub-group 3 ($M^{3+}$=Sc, Y, La: $M^{3+}(OMe)_3$, $M^{3+}(OEt)_3$, $M^{3+}(OC_3H_7)_3$, $M^{3+}(OC_4H_9)_3$, $cpM^{3+}(Cl)_2$, cp $cpM^{3+}(OMe)_2$, $CPM^{3+}(OEt)_2$, $cpM^{3+}(NMe_2)_2$ where cp=cyclopentadienyl), halides, sulfides, amides, thiolates or alcoholates of main group 4 ($M^{4+}$=Si, Ge, Sn, Pb: $M^{4+}(OMe)_4$, $M^{4+}(OEt)_4$, $M^{4+}(OC_3H_7)_4$, $M^{4+}(OC_4H_9)_4$; $M^{2+}$=Sn, Pb: $M^{2+}(OMe)_2$, $M^{2+}(OEt)_2$, $M^{2+}(OC_3H_7)_2$, $M^{2+}(OC_4H_9)_2$) tin dilaurate, tin diacetate, $Sn(OBu)_2$, halides, oxides, sulfides, imides, alcoholates, amides, thiolates and combinations of the substituent classes mentioned with multiple bonded ligands on compounds of sub-group 4 ($M^{4+}$=Ti, Zr, Hf: $(M^{4+}(F)_4$, $M^{4+}(Cl)_4$, $M^{4+}(Br)_4$, $M^{4+}(I)_4$; $M^{4+}(OMe)_4$, $M^{4+}(OEt)_4$, $M^{4+}(OC_3H_7)_4$, $M^{4+}(OC_4H_9)_4$, $cp_2Ti(Cl)_2$, $cp_2Zr(Cl)_2$, $cp_2Hf(Cl)_2$, $cp_2Ti(OMe)_2$, $cp_2Zr(OMe)_2$, $cp_2Hf(OMe)_2$, $cpTi(Cl)_3$, $cpZr(Cl)_3$, $cpHf(Cl)_3$; $cpTi(OMe)_3$, $cpZr(OMe)_3$, $cpHf(OMe)_3$, $M^{4+}(NMe_2)_4$, $M^{4+}(NEt_2)_4$, $M^{4+}(NHC_4H_9)_4$), halides, oxides, sulfides, imides, alcoholates, amides, thiolates and combinations of the substituent classes mentioned with multiple bonded ligands on compounds of sub-group 5 ($M^{5+}$, $M^{4+}$ or $M^{3+}$=V, Nb, Ta: $M^{5+}(OMe)_5$, $M^{5+}(OEt)_5$, $M^{5+}(OC_3H_7)_5$, $M^{5+}(OC_4H_9)_5$, $M^{3+}O(OMe)_3$, $M^{3+}O(OEt)_3$, $M^{3+}O(OC_3H_7)_3$, $M^{3+}O(OC_4H_9)_3$, $cpV(OMe)_4$, $cpNb(OMe)_3$, $cpTa(OMe)_3$; $cpV(OMe)_2$, $cpNb(OMe)_3$, $cpTa(OMe)_3$), halides, oxides, sulfides, imides, alcoholates, amides, thiolates and combinations of the substituent classes mentioned with multiple bonded ligands on compounds of sub-group 6 ($M^{6+}$, $M^{5+}$ or $M^{4+}$=Cr, Mo, W: $M^{6+}(OME)_6$, $M^{6+}(OEt)_6$, $M^{6+}(OC_3H_7)_6$, $M^{6+}(OC_4H_9)_6$, $M^{6+}O(OMe)_4$, $M^{6+}O(OEt)_4$, $M^{6+}O$ $(OC_3H_7)_4$, $M^{6+}O(OC_4H_9)_4$, $M^{6+}O_2(OMe)_2$, $M^{6+}O_2(OEt)_2$, $M^{6+}O_2(OC_3H_7)_2$, $M^{6+}O_2(OC_4H_9)_2$, $M^{6+}O_2(OSiMe_3)_2$) or halides, oxides, sulfides, imides, alcoholates, amides, thiolates and combinations of the substituent classes mentioned with multiple bonded ligands on compounds of sub-group 7 ($M^{7+}$, $M^{6+}$, $M^{5+}$ or $M^{4+}$=Mn, Re: $M^{7+}O$ $(OMe)_5$, $M^{7+}O$ $(OEt)_5$, $M^{7+}O(OC_3H_7)_5$, $M^{7+}O(OC_4H_9)_5$, $M^{7+}O_2(OMe)_3$, $M^{7+}O_2(OEt)_3$, $M^{7+}O_2(OC_3H_7)_3$, $M^{7+}O_2(OC_4H_9)_3$, $M^{7+}O_2(OSiMe_3)_3$, $M^{7+}O_3(OSiMe_3)$, $M^{7+}O_3(CH_3)$).

The metal and transition metal can have a free coordination site on the metal.

Metal or transition metal compounds which are formed by addition of water to hydrolysable metal or transition metal compounds can also be used as catalysts.

In a particular embodiment, titanates, such as, for example, tetra-n-butyl orthotitanate or tetra-iso-propyl orthotitanate, can be used as catalysts.

The reaction can be carried out at temperatures of between 20 and 200° C., preferably between 50 and 170° C., particularly preferably between 80 and 150° C. To avoid condensation reactions, it may be advantageous to carry out the reaction in an anhydrous environment, ideally in an inert gas atmosphere.

The reaction can be carried out under normal pressure or reduced pressure. The reaction can be carried out continuously or discontinuously.

The organosilicon compounds according to the invention can be used as adhesion promoters between inorganic materials, for example glass fibres, metals, oxidic fillers and silicas, and organic polymers, for example thermosets, thermoplastics or elastomers, or as crosslinking agents and surface-modifying agents. The organosilicon compounds according to the invention can be used as coupling reagents in rubber mixtures comprising fillers, for example tyre treads.

The invention also provides rubber mixtures comprising
(A) a rubber or a mixture of rubbers,
(B) a filler and
(C) at least one mercaptosilane of the general formula I.

Natural rubber and/or synthetic rubbers can be used as the rubber. Preferred synthetic rubbers are described, for example, in W. Hofmann, Kautschuktechnologie, Genter Verlag, Stuttgart 1980. They can be, inter alia,
  polybutadiene (BR),
  polyisoprene (IR),
  styrene/butadiene copolymers, for example emulsion SBR (E-SBR) or solution SBR (S-SBR), preferably having styrene contents of from 1 to 60 wt. %, particularly preferably 5 to 50 wt. % (SBR),
  chloroprene (CR)
  isobutylene/isoprene copolymers (IIR),
  butadiene/acrylonitrile copolymers having acrylonitrile contents of from 5 to 60, preferably 10 to 50 wt. % (NBR),
  partly hydrogenated or completely hydrogenated NBR rubber (HNBR)
  ethylene/propylene/diene copolymers (EPDM)
  the abovementioned rubbers which additionally have functional groups, such as e.g. carboxyl, silanol or epoxide groups, for example epoxidized NR, carboxy-functionalized NBR or silanol- (—SiOH) or siloxy-functionalized (—Si—OR) SBR,
and mixtures of these rubbers.

In a preferred embodiment, the rubbers can be vulcanizable with sulfur. Anionically polymerized S-SBR rubbers (solution SBR) having a glass transition temperature above −50° C. and mixtures thereof with diene rubbers can be employed in particular for the production of car tyre treads. S-SBR rubbers in which the butadiene content has a vinyl content of more than 20 wt. % can particularly preferably be employed. S-SBR rubbers in which the butadiene content has a vinyl content of more than 50 wt. % can very particularly preferably be employed.

Mixtures of the abovementioned rubbers which have an S-SBR content of more than 50 wt. %, particularly preferably more than 60 wt. %, can preferably be employed.

The following fillers can be employed as fillers for the rubber mixtures according to the invention:

Carbon blacks: The carbon blacks to be used here are prepared by the flame black, furnace, gas black or thermal process and have BET surface areas of from 20 to 200 m$^2$/g. The carbon blacks can optionally also contain heteroatoms, such as, for example, Si.

Amorphous silicas, prepared, for example, by precipitation of solutions of silicates or flame hydrolysis of silicon halides having specific surface areas of from 5 to 1,000 m$^2$/g, preferably 20 to 400 m$^2$/g (BET surface area) and having primary particle sizes of from 10 to 400 nm. The silicas can optionally also be in the form of mixed oxides with other metal oxides, such as Al, Mg, Ca, Ba, Zn and titanium oxides.

Synthetic silicates, such as aluminium silicate, alkaline earth metal silicates, such as magnesium silicate or calcium silicate, having BET surface areas of from 20 to 400 m$^2$/g and primary particle diameters of from 10 to 400 nm.

Synthetic or natural aluminium oxides and hydroxides

Natural silicates, such as kaolin and other naturally occurring silicas.

Glass fibres and glass fibre products (mats, strands) or glass microbeads.

Preferably, amorphous silicas prepared by precipitation from solutions of silicates, having BET surface areas of from 20 to 400 m$^2$/g, particularly preferably 100 m$^2$/g to 250 m$^2$/g, are employed in amounts of from 5 to 150 parts by wt., in each case based on 100 parts of rubber.

The fillers mentioned can be employed by themselves or as a mixture.

The rubber mixtures can comprise 5 to 150 parts by wt. of filler (B) and 0.1 to 25 parts by wt., preferably 2 to 20 parts by wt., particularly preferably 5 to 15 parts by wt. of mercaptosilane of the formula I (C), the parts by wt. being based on 100 parts by wt. of rubber.

The mercaptosilane of the formula I can be added to the mixing process either in the pure form or in a form absorbed on an inert organic or inorganic support, as well as in a form prereacted with an organic or inorganic support. Preferred support materials are precipitated or pyrogenic silicas, waxes, thermoplastics, natural or synthetic silicates, natural or synthetic oxides, specifically aluminium oxide, or carbon blacks. The mercaptosilane of the formula I can furthermore also be added to the mixing process in a form prereacted with the filler to be employed.

The rubber mixtures can additionally comprise silicone oil and/or alkylsilane.

The rubber mixtures according to the invention can comprise further known rubber auxiliaries, such as, for example, crosslinking agents, vulcanization accelerators, reaction accelerators or retardants, anti-ageing agents, stabilizers, processing auxiliaries, plasticizers, waxes or metal oxides, and optionally activators, such as triethanolamine, polyethylene glycol or hexanetriol.

The rubber auxiliaries can be employed in conventional amounts, which depend, inter alia, on the intended use. Conventional amounts are, for example, amounts of from 0.1 to 50 wt. %, based on the rubber.

Sulfur or organic sulfur donors can be employed as crosslinking agents.

The rubber mixtures according to the invention can comprise further vulcanization accelerators. For example, mercaptobenzothiazoles, sulfenamides, guanidines, dithiocarbamates, thioureas, thiocarbonates and zinc salts thereof, such as e.g. zinc dibutyldithiocarbamate, can be employed as suitable vulcanization accelerators.

The rubber mixtures according to the invention can preferably additionally comprise (D) a thiuram sulfide and/or carbamate accelerator and/or the corresponding zinc salts,
(E) a nitrogen-containing co-activator,
(F) optionally further rubber auxiliaries and
(G) optionally further accelerators, the weight ratio of accelerator (D) to nitrogen-containing co-activator (E) being equal to or greater than 1.

The rubber mixtures according to the invention can comprise (D) tetrabenzylthiuram disulfide or tetramethylthiuram disulfide in at least 0.25 part by weight, based on 100 parts by weight of rubber, (E) diphenylguanidine in no more than 0.25 part by weight, based on 100 parts by weight of rubber, and (G) cyclohexyl- or dicyclohexylsulfenamide in more parts by weight than (D).

Preferably, sulfenamides can be employed together with guanidines and thiurams, particularly preferably cyclohexylsulfenamide or dicyclohexylsulfenamide together with diphenylguanidine and tetrabenzylthiuram disulfide or tetramethylthiuram disulfide.

The vulcanization accelerators and sulfur can be employed in amounts of from 0.1 to 10 wt. %, preferably 0.1 to 5 wt. %, based on the rubber employed. Particularly preferably, sulfur and sulfenamides can be employed in amounts of from 1 to 4 wt. %, thiurams in amounts of from 0.2 to 1 wt. % and guanidines in amounts of from 0 wt. % to 0.5 wt. %.

The invention also provides a process for the preparation of the rubber mixtures according to the invention, which is characterized in that the rubber or the mixture of rubbers (A), the filler (B), at least one mercaptosilane of the general formula I according to the invention (C) and optionally further rubber auxiliaries are mixed in a mixing unit.

The mixing of the rubbers with the filler, optionally rubber auxiliaries and the mercaptosilanes according to the invention can be carried out in conventional mixing units, such as roll mills, internal mixers and mixing extruders.

Such rubber mixtures can conventionally be prepared in internal mixers, the rubbers, the filler, the mercaptosilanes according to the invention and the rubber auxiliaries first being mixed in at 100 to 170° C. in one or several successive thermomechanical mixing stages. The sequence of addition and the time of addition of the individual components can have a decisive effect on the resulting mixture properties here. The crosslinking chemicals can conventionally be added to the rubber mixture obtained in this way in an internal mixer or on a roll mill at 40 to 110° C. and the mixture can be processed to the so-called crude mixture for the subsequent process steps, such as, for example, shaping and vulcanization.

The vulcanization of the rubber mixtures according to the invention can be carried out at temperatures of from 80 to 200° C., preferably 130 to 180° C., optionally under a pressure of from 10 to 200 bar.

The rubber mixtures according to the invention can be used for the production of shaped articles, for example for the production of pneumatic tyres, tyre treads, cable sheathings, hoses, drive belts, conveyor belts, roller coverings, tyres, shoe soles, sealing elements, such as, for example, sealing rings, and damping elements.

The invention also provides shaped articles obtainable from the rubber mixture according to the invention by vulcanization.

The mercaptosilanes according to the invention have the advantage that even with short, commercially acceptable mixing times in rubber, the amplification ratio is high, the hysteresis loss is low and the abrasion resistance is high, and at the same time the alcohol emission is reduced compared with trimethoxy- and triethoxy-substituted mercaptosilanes.

EXAMPLES

Example 1

59.63 g (0.25 mol) 3-mercaptopropyltriethoxysilane (VP Si 263 from Degussa AG), 212.92 g (0.50 mol) of an ethoxylated alcohol $R^1H$, where $R^5$ is $CH_2$—$CH_2$, $R^6$ is an unsubstituted, monovalent alkyl group comprising 13 C atoms and m is on average 5 (Lutensol TO 5 from BASF AG) and 30 µl titanium tetrabutylate are weighed into a 500 ml four-necked flask with a distillation bridge, KPG stirrer and thermometer at room temperature under nitrogen. The mixture is heated to 140° C. The ethanol formed is distilled off continuously. After 35 min, the reduced pressure is adjusted to 640 mbar and reduced to 50 mbar in the course of 3 h. The reaction is ended after 3 h and 35 min. 245.37 g (98.6%) of a cloudy and slightly yellow product are obtained. An average degree of transesterification of 2.0 is obtained from $^1H$-NMR spectroscopy. The distribution of the long-chain branched alkyl polyethers on the Si can be determined from $^{13}C$-NMR.

Example 2 (Comparison Example)

2,925.3 g 3-mercaptopropyltriethoxysilane, 4,753.4 g of an alcohol mixture comprising 72% dodecanol and 28% tetradecanol and 30 µl titanium tetrabutylate are weighed into a 4 l four-necked flask with a distillation bridge, KPG stirrer and thermometer at room temperature under nitrogen. The mixture is heated to 110° C. The ethanol formed is distilled off continuously. After 2 h, the reduced pressure is reduced continuously to 50 mbar in the course of 3 h. The reaction is ended when 1,140 ml ethanol are removed from the reaction mixture. 6.47 kg (98.6%) of a slightly yellow liquid are obtained. An average degree of transesterification of 2.0 is obtained from $^1H$-NMR spectroscopy.

Example 3 (Comparison Example)

150.02 g (0.63 mol) 3-mercaptopropyltriethoxysilane, 151.2 g (1.26 mol) diethylene glycol monomethyl ether and 75 µl titanium tetrabutylate are weighed into a 500 ml three-necked flask with an intensive condenser, stirrer and thermometer at room temperature under nitrogen. The mixture is heated to 80° C. The ethanol formed is then removed under a reduced pressure of 3 mbar.

The reaction is ended after 8 h. 237.84 g (97.6%) of a clear and slightly yellow product are obtained. An average degree of transesterification of 2.0 is obtained from $^1H$-NMR spectroscopy.

Example 4 (Comparison Example)

180.01 g (0.75 mol) 3-mercaptopropyltriethoxysilane, 136.05 g (1.51 mol) ethylene glycol monoethyl ether and 90 µl titanium tetrabutylate are weighed into a 1 l three-necked flask with an intensive condenser, stirrer and thermometer at room temperature under nitrogen. The mixture is heated to 60° C. and the ethanol formed is distilled off under a reduced pressure of 200 mbar. After 1 h, the temperature is increased to 120° C. in the course of 16 h and the reduced pressure is reduced to 40 mbar.

The reaction is ended after 17 h. 244.04 g (99.6%) of a cloudy and slightly yellow product are obtained. An average degree of transesterification of 2.0 is obtained from $^1H$-NMR spectroscopy.

Example 5 (Comparison Example)

59.79 g (0.25 mol) 3-mercaptopropyltriethoxysilane, 161.42 g (0.50 mol) of an ethoxylated alcohol $R^1H$, where $R^5$ is $CH_2$—$CH_2$, $R^6$ is an unsubstituted, monovalent alkyl group comprising 6 C atoms and m is on average 5 (Aduxol NHX-05B from Schärer+Schläpfer) and 30 µl titanium tetrabutylate are weighed into a 500 ml three-necked flask with a distillation bridge, stirrer and thermometer at room temperature under nitrogen. The mixture is heated to 140° C. and the ethanol formed is initially removed under a reduced pressure of 885 mbar. The reduced pressure is reduced to 19 mbar in the course of 5 h The reaction can be ended after 5.8 h.

193.30 g (97.73%) of a cloudy and slightly yellow product are obtained. An average degree of transesterification of 2.2 is determined from $^1H$-NMR spectroscopy.

Example 6 (Comparison Example)

59.62 g (0.25 mol) 3-mercaptopropyltriethoxysilane, 189.03 g (0.50 mol) of an ethoxylated alcohol $R^1H$, where $R^5$ is $CH_2$—$CH_2$, $R^6$ is an unsubstituted, monovalent alkyl group comprising 10 C atoms and m is on average 5 (Imbentin AG 100/35 from Kolb, Switzerland) and 30 µl titanium tetrabutylate are weighed into a 500 ml three-necked flask with an intensive condenser, stirrer and thermometer at room temperature under nitrogen. The mixture is heated to 140° C. and the ethanol formed is removed under a reduced pressure of 887 mbar. The reduced pressure is reduced to 35 mbar during the reaction. The reaction can be ended after 3.5 h.

220.96 g (97.96%) of a cloudy and slightly yellow product are obtained. An average degree of transesterification of 1.9 is obtained from $^1H$-NMR spectroscopy.

Example 7 (Comparison Example)

59.79 g (0.25 mol) 3-mercaptopropyltriethoxysilane, 161.42 g (0.50 mol) of an ethoxylated alcohol $R^1H$, where $R^5$ is $CH_2$—$CH_2$, $R^6$ is an unsubstituted, monovalent alkyl group comprising 10 C atoms and m is on average 20 (Imbentin AG 100/200 from Kolb) and 30 µl titanium tetrabutylate are weighed into a 500 ml three-necked flask with a distillation bridge, stirrer and thermometer at room temperature under nitrogen. The mixture is heated to 140° C. and the ethanol formed is initially removed under a reduced pressure of 887 mbar. The reduced pressure is reduced to 12 mbar in the course of 7.5 h. The reaction can be ended after 7.5 h.

542.56 g (97.96%) of a solid, cloudy and slightly yellow product are obtained. An average degree of transesterification of 1.9 is determined from $^{29}Si$-NMR spectroscopy.

Example 8

141.4 g (0.593 mol) 3-mercaptopropyltriethoxysilane, 251.7 g (0.593 mol) of an ethoxylated alcohol $R^1H$, where $R^5$ is $CH_2$—$CH_2$, $R^6$ is an unsubstituted, monovalent alkyl group comprising 13 C atoms and m is on average 5 (Lutensol TO 5 from BASF AG) and 70 mg titanium tetrabutylate are weighed into a 500 ml four-necked flask with a distillation bridge, magnetic stirrer and thermometer at room temperature under nitrogen. The mixture is heated to 140° C. The ethanol formed is removed continuously under a reduced pressure of 1,013 mbar. After 1 h, the reduced pressure is reduced continuously to 10 mbar in the course of 3 h. The reaction is ended after 455 min in total. 359.9 g (98.4%) of a cloudy and slightly red product are obtained. An average degree of transesterification of 1 is obtained from $^1$H-NMR spectroscopy.

Example 9

1,038.2 g (4.35 mol) 3-mercaptopropyltriethoxysilane, 3,663.3 g (8.71 mol) of an ethoxylated alcohol $R^1H$, where $R^5$ is $CH_2$—$CH_2$, $R^6$ is an unsubstituted, monovalent alkyl group comprising 13 C atoms and m is on average 5 (Lutensol TO 5 from BASF AG) and 519 mg titanium tetrabutylate are weighed into a 10 l four-necked flask with a distillation bridge, KPG stirrer and thermometer at room temperature under nitrogen. The mixture is heated to 140° C. The ethanol formed is distilled off continuously. After 1 h, the reduced pressure is reduced to 50 mbar in the course of 430 min. The reaction is ended after 625 min in total. 4,252.0 g (98.9%) of a cloudy and slightly orange liquid are obtained. An average degree of transesterification of 2.0 is obtained from $^{13}$C-NMR spectroscopy.

Example 10

61.7 g (0.259 mol) 3-mercaptopropyltriethoxysilane, 329.5 g (0.776 mol) of an ethoxylated alcohol $R^1H$, where $R^5$ is $CH_2$—$CH_2$, $R^6$ is an unsubstituted, monovalent alkyl group comprising 13 C atoms and m is on average 5 (Lutensol TO 5 from BASF AG) and 30 mg titanium tetrabutylate are weighed into a 500 ml four-necked flask with a distillation bridge, KPG stirrer and thermometer at room temperature under nitrogen. The mixture is heated to 140° C. The ethanol formed is removed continuously first under normal pressure and, after 1 h, under a reduced pressure of 800 mbar. After a further 2 h, the reduced pressure is lowered to 50 mbar in the course of 3 h. The reaction is ended after 12 h. 352.7 g (99.1%) of a cloudy and colourless product are obtained. An average degree of transesterification of approx. 3 is obtained from $^{13}$C-NMR spectroscopy.

Example 11

59.64 g 3-mercaptopropyltriethoxysilane having an oligomer content of approx. 30 mol %, 212.2 g (0.50 mol) of an ethoxylated alcohol $R^1H$, where $R^5$ is $CH_2$—$CH_2$, $R^6$ is an unsubstituted, monovalent alkyl group comprising 13 C atoms and m is on average 5 (Lutensol TO 5 from BASF AG) and 30 µl titanium tetrabutylate are weighed into a 500 ml three-necked flask with a distillation bridge, stirrer and thermometer at room temperature under nitrogen. The mixture is heated to 140° C. and the ethanol formed is initially removed under normal pressure. After 45 min, distillation is carried out under a reduced pressure of 600 mbar. The reduced pressure is reduced to 40 mbar in the course of 5 h. The reaction can be ended after 6 h in total. 233.4 g (96.0%) of a cloudy and slightly orange liquid are obtained. An average degree of transesterification of 2.5 is determined from $^{29}$Si-NMR spectroscopy.

Example 12

The recipe used for the rubber mixtures is given in the following Table 1. The unit phr here means parts by weight per 100 parts of the crude rubber employed.

The silane according to the invention used for Example Mixture I is the mercaptosilane prepared in Example 1. Its structure corresponds to the general formula I, wherein $R^1$ is an alkyl polyether group —O—$(CH_2$—$CH_2$—$O)_m$—$C_nH_{2n+1}$ where m is on average 5 and n is 13, $R^2$ is a mixture of $R^1$ and ethoxy groups in the ratio of 1:1, $R^3$ is the trimethylene group —$CH_2$—$CH_2$—$CH_2$— and $R^4$ is H.

The silane Si 69 used for Reference Mixture I is commercially obtainable from Degussa AG. The silane used for Reference Mixture II is the mercaptosilane from Example 2 of the general formula III

$$(R^{12})_p(R^{13})_{3-p}Si—(CH_2)_3—SH \qquad III$$

where $R^{12}$=ethoxy and $R^{13}$ is a mixture of dodecoxy and tetradecoxy, p is on average 1 and the ratio of dodecoxy to tetradecoxy is in the weight ratio of 72:28.

In Reference Mixtures I and II and Example Mixture I, the base mixtures (1st+2nd stage) are identical apart from the silanes used. Reference Mixture I differs from Reference Mixture II in the amounts of sulfur, accelerator DPG and ultra-accelerator TBzTD (3rd stage) employed. Reference Mixture I contains Si 69, a polysulfidic silane. The accelerator system must be adapted to the silane used. Since Si 69 is a sulfur donor and the mercaptosilane is not a sulfur donor, for compensation less sulfur is employed in Reference Mixture II and in Example Mixture I according to the invention than in Reference Mixture I with Si 69.

TABLE 1

| Substance | Amount [phr] Reference Mixture I | Amount [phr] Reference Mixture II | Amount [phr] Example Mixture 1 |
|---|---|---|---|
| 1st stage | | | |
| Buna VSL 5025-1 | 96 | 96 | 96 |
| Buna CB 24 | 30 | 30 | 30 |
| Ultrasil 7000 GR | 80 | 80 | 80 |
| ZnO | 3 | 3 | 3 |
| Stearic acid | 2 | 2 | 2 |
| Naftolen ZD | 10 | 10 | 10 |
| Vulkanox 4020 | 1.5 | 1.5 | 1.5 |
| Protector G 3108 | 1 | 1 | 1 |
| Si 69 | 10 | — | — |
| Silane from Example 2 | — | 10 | — |
| Silane from Example 1 | — | — | 10 |
| 2nd stage Batch stage 1 | | | |
| 3rd stage Batch stage 2 | | | |
| Vulkacit D | 2 | 0.25 | 0.25 |
| Perkacit TBzTD | 0.2 | 0.5 | 0.5 |
| Vulkacit CZ | 1.5 | 1.5 | 1.5 |
| Sulfur | 1.5 | 2.2 | 2.2 |

The polymer VSL 5025-1 is an SBR copolymer from Bayer AG polymerized in solution and having a styrene content of 25 wt. % and a butadiene content of 75 wt. %. The copolymer comprises 37.5 phr oil and has a Mooney viscosity (ML 1+4/100° C.) of 50.

The polymer Buna CB 24 is a cis-1,4-polybutadiene (neodymium type) from Bayer AG having a cis-1,4 content of at least 96% and a Mooney viscosity of 44±5.

Ultrasil 7000 GR is a readily dispersible silica from Degussa AG and has a BET surface area of 170 m$^2$/g.

The coupling reagent Si 69, a bis-(triethoxysilylpropyl) polysulfide, is a product from Degussa AG.

Naftolen ZD from Chemetall is used as the aromatic oil, Vulkanox 4020 is 6PPD from Bayer AG, and Protector G3108 is an anti-ozonant wax from Paramelt B.V. Vulkacit D (DPG) and Vulkacit CZ (CBS) are commercial products from Bayer AG. Perkacit TBzTD (tetrabenzylthiuram disulfide) is a product from Flexsys N.V.

The rubber mixture is prepared in three stages in an internal mixer in accordance with Table 2, economically acceptable mixing times being used.

TABLE 2

| Stage 1 | |
|---|---|
| Settings | |
| Mixing unit | Werner & Pfleiderer |
| Friction | 1:1 |
| Speed | 60 min$^{-1}$ |
| Plunger pressure | 5.5 bar |
| Empty volume | 1.6 L |
| Filling level | 0.56 |
| Flow temp. | 70° C. |
| Mixing operation | |
| 0 to 1 min | Buna VSL 5025-1 + Buna CB 24 |
| 1 to 2 min | ½ Ultrasil 7000 GR, ZnO, stearic acid, Naftolen ZD, silane |
| 2 to 3 min | ½ Ultrasil 7000 GR, Vulkanox 4020, Protector G3108 |
| 3 to 4 min | mix and deliver |
| Batch temp. | 140-150° C. |
| Storage | 24 h at room temperature |
| Stage 2 | |
| Settings | |
| Mixing unit | as in stage 1 except: |
| Speed | 70 min$^{-1}$ |
| Filling level | 0.53 |
| Flow temp. | 80° C. |
| Mixing operation | |
| 0 to 2 min | break up batch stage 1 |
| 2 to 3 min | maintain batch temperature 145-150° C. by varying speed |
| 3 min | deliver |
| Batch temp. | 145-150° C. |
| Storage | 4 h at room temperature |
| Stage 3 | |
| Settings | |
| Mixing unit | as in stage 1 except |
| Speed | 40 min$^{-1}$ |
| Filling level | 0.50 |
| Flow temp. | 50° C. |
| Mixing operation | |
| 0 to 2 min | Batch stage 2 + Vulkacit CZ + Vulkacit D + Perkacit TBzTD + sulfur |

TABLE 2-continued

| 2 min | deliver and form skin on laboratory roll mill (diameter 200 mm, length 450 mm, flow temperature 50° C.) Homogenization: cut in 5* left, 5* right and fold over turn over 5* for a narrow roll nip (3 mm) and 5* for a wide roll nip (6 mm) then draw out a skin |
|---|---|
| Batch temp. | 90-100° C. |

The general process for the preparation of rubber mixtures and vulcanisates thereof is described in "Rubber Technology Handbook", W. Hofmann, Hanser Verlag 1994.

The rubber testing is carried out in accordance with the test methods described in Table 3.

TABLE 3

| Physical testing | Standard/Conditions |
|---|---|
| ML 1 + 4, 100° C. (3rd stage) | DIN 53523/3, ISO 667 |
| Partial vulcanization properties, 130° C. | DIN 53523/4, ISO 667 |
| Vulcameter test, 165° C. | DIN 53529/3, ISO 6502 |
| D$_{max}$ − D$_{min}$ | |
| t10% | |
| t80% − t20% | |
| Tensile test on ring, 23° C. | DIN 53504, ISO 37 |
| Tensile strength | |
| Moduli | |
| Elongation at break | |
| Shore A hardness, 23° C. | DIN 53 505 |
| Ball rebound, 60° C. | DIN EN ISO 8307 steel ball 19 mm, 28 g |
| DIN abrasion, 10N force | DIN 53 516 |
| Viscoelastic properties | DIN 53 513, ISO 2856 |
| 0 and 60° C., 16 Hz, 50N preliminary force and 25N amplitude force | |
| Complex E* modulus (MPa) | |
| Loss factor tan δ (—) | |

The rubber data for the mixture and vulcanisate are given in Table 4.

TABLE 4

| Feature: | Unit: | Reference Mixture I | Reference Mixture II | Example Mixture 1 |
|---|---|---|---|---|
| Crude mixture data | | | | |
| ML(1 + 4) at 100° C., 3rd stage | [MU] | 63 | 64 | 65 |
| Dmax − Dmin | [dNm] | 21.6 | 14.6 | 17.9 |
| t 10% | [min] | 1.5 | 0.5 | 1.2 |
| t 80% − t 20% | [min] | 3.1 | 9.0 | 1.1 |
| Scorch time, t5 | [min] | 25.68 | 3.35 | 9.13 |
| Scorch time, t35 | [min] | 33.60 | 4.77 | 14.07 |
| Vulcanisate data | | | | |
| Tensile strength | [MPa] | 13.5 | 10.0 | 14.7 |
| Modulus 100% | [MPa] | 2.3 | 1.7 | 2.1 |
| Modulus 300% | [MPa] | 10.6 | — | 12.2 |
| Modulus 300%/100% | [—] | 4.6 | — | 5.8 |
| Elongation at break | [%] | 355 | 290 | 340 |
| Shore A hardness | [SH] | 67 | 57 | 61 |
| Ball rebound, 60° C. | [%] | 64.9 | 70.7 | 73.3 |

TABLE 4-continued

| Feature: | Unit | Reference Mixture I | Reference Mixture II | Example Mixture 1 |
|---|---|---|---|---|
| DIN abrasion | [mm³] | 99 | 56 | 77 |
| Dyn. extension modulus E* 0° C. | [MPa] | 18.4 | 10.1 | 11.2 |
| Dyn. extension modulus E* 60° C. | [MPa] | 9.1 | 7.1 | 7.6 |
| Loss factor tan δ, 0° C. | [—] | 0.381 | 0.281 | 0.317 |
| Loss factor tan δ, 60° C. | [—] | 0.103 | 0.080 | 0.064 |

It can be seen from the results in Table 4 that at the mixing times used here the mixtures comprising the silane according to the invention are superior to the reference mixtures. Reference Mixture I, comprising Si 69, shows the poorest profile of values. Reference Mixture I has a low modulus 300%/100% value, which is a measure of the amplification ratio. Reference Mixture I has the lowest ball rebound and the highest tan δ, 60° C., which indicates a high rolling resistance. Furthermore, the abrasion is the worst.

In Reference Mixture II the abrasion is indeed improved significantly due to the higher amplification ratio.

However, the crude mixture data drop significantly. With a scorch time t35 of less than 5 min and a t10% time of 0.5 min, this mixture is not processable.

Only Example Mixture I with the silane according to the invention shows a high amplification ratio here with simultaneously ensured processing. The scorch time t35 is prolonged by approx. 10 min compared with Reference Mixture II, and the t10% is more than doubled. In contrast to Reference Mixture II, Example Mixture I is processable. At the same time, the ball rebound and tan δ, 60° C. show the low hysteresis loss. The DIN abrasion is reduced by 13% compared with Reference Mixture I with the commercial silane Si 69.

Example 13

In this example, Example Mixture I, comprising the silane according to the invention from Example 1, is compared with mixtures comprising mercaptosilanes which are substituted by alkyl polyether groups in which the substituted or unsubstituted alkyl radical is built up from less than 11 carbon units.

The silane used for Reference Mixture III is the mercaptosilane from Example 3 of the general formula IV $$(R^{12})_p(R^{14})_{3-p}Si-(CH_2)_3-SH \qquad IV$$

where $R^{12}$=ethoxy and $R^{14}$=alkyl polyether groups —O—$(CH_2-CH_2-O)_m-C_nH_{2n+1}$, where m=2, n=1 and p is on average 1.

The silane used for Reference Mixture IV is the mercaptosilane from Example 4 of the general formula IV, where $R^{12}$=ethoxy and $R^{14}$=alkyl polyether groups —O—$(CH_2-CH_2-O)_m-C_nH_{2n+1}$, where m=1, n=2 and p is on average 1.

The silane used for Reference Mixture V is the mercaptosilane from Example 5 of the general formula IV, where $R^{12}$=ethoxy and $R^{14}$=alkyl polyether groups —O—$(CH_2-CH_2-O)_m-C_nH_{2n+1}$, where m is on average 5, n=6 and p is on average 0.8.

The silane used for Reference Mixture VI is the mercaptosilane from Example 6 of the general formula IV, where $R^{12}$=ethoxy and $R^{14}$=alkyl polyether groups —O—$(CH_2-CH_2-O)_m-C_nH_{2n+1}$, where m is on average 5, n=10 and p is on average 1.1.

The recipe used for the rubber mixtures is given in the following Table 5. In this context, the unit phr again means parts by weight per 100 parts of the crude rubber employed.

TABLE 5

| Substance | Amount [phr] Reference Mixture III | Amount [phr] Reference Mixture IV | Amount [phr] Reference Mixture V | Amount [phr] Reference Mixture VI | Amount [phr] Example Mixture I |
|---|---|---|---|---|---|
| 1st stage | | | | | |
| Buna VSL 5025-1 | 96 | 96 | 96 | 96 | 96 |
| Buna CB 24 | 30 | 30 | 30 | 30 | 30 |
| Ultrasil 7000GR | 80 | 80 | 80 | 80 | 80 |
| ZnO | 3 | 3 | 3 | 3 | 3 |
| Stearic acid | 2 | 2 | 2 | 2 | 2 |
| Naftolen ZD | 10 | 10 | 10 | 10 | 10 |
| Vulkanox 4020 | 1.5 | 1.5 | 1.5 | 1.5 | 1.5 |
| Protector G3108 | 1 | 1 | 1 | 1 | 1 |
| Silane from Example 3 | 10 | — | — | — | — |
| Silane from Example 4 | — | 10 | — | — | — |
| Silane from Example 5 | — | — | 10 | — | — |
| Silane from Example 6 | — | — | — | 10 | — |
| Silane from Example 1 | — | — | — | — | 10 |
| 2nd stage Batch stage 1 | | | | | |
| 3rd stage Batch stage 2 | | | | | |
| Vulkacit D | 0.25 | 0.25 | 0.25 | 0.25 | 0.25 |
| Perkacit TBzTD | 0.5 | 0.5 | 0.5 | 0.5 | 0.5 |

TABLE 5-continued

| Substance | Amount [phr] Reference Mixture III | Amount [phr] Reference Mixture IV | Amount [phr] Reference Mixture V | Amount [phr] Reference Mixture VI | Amount [phr] Example Mixture I |
|---|---|---|---|---|---|
| Vulkacit CZ | 1.5 | 1.5 | 1.5 | 1.5 | 1.5 |
| Sulfur | 2.2 | 2.2 | 2.2 | 2.2 | 2.2 |

The rubber mixture is prepared in three stages in an internal mixer in accordance with Table 2.

The rubber testing is carried out in accordance with the test methods described in Table 3.

Under the mixing conditions used, Example Mixture I shows the best processing properties, as emerges from the rubber data for the crude mixtures given in Table 6.

TABLE 6

| Feature: | Unit: | Reference Mixture III | Reference Mixture IV | Reference Mixture V | Reference Mixture VI | Example Mixture 1 |
|---|---|---|---|---|---|---|
| Crude mixture data | | | | | | |
| ML(1 + 4) at 100° C., 3rd stage | [MU] | not measurable | not measurable | 78 | 66 | 65 |
| Dmax − Dmin | [dNm] | 8.9 | 8.8 | 15.3 | 16.4 | 17.9 |
| t 10% | [min] | 0.4 | 0.4 | 0.5 | 1.0 | 1.2 |
| t 80% − t 20% | [min] | 1.8 | 5.5 | 0.8 | 1.0 | 1.1 |
| Scorch time, t5 | [min] | 6.23 | 7.92 | 2.93 | 6.26 | 9.13 |
| Scorch time, t35 | [min] | 12.04 | 15.10 | 4.96 | 10.66 | 14.07 |

The results show that when the reference silanes from Example 3 and 4 with the shortest alkyl polyether groups are used, mixtures which can neither be processed nor employed are obtained. They have the shortest t10% times and the Mooney viscosity cannot even be determined. From the small differences in the torques in the MDR it can be seen that these Reference Mixtures III and IV are not vulcanizable. Only if longer-chain alkyl polyether groups are used is an acceptable crosslinking yield obtained, which is reflected in the significant increase in the differences in the torques. Needless to say, it is found that only the example mixture with the mercaptosilane according to the invention has acceptable processing properties. It shows the lowest Mooney viscosity, the longest t10% and the longest Mooney scorch time. The t10% time is prolonged by 20% compared with Reference Mixture VI and even by 140% compared with Reference Mixture V. The Mooney scorch time t35 is prolonged by 32% compared with Reference Mixture VI and by 184% compared with Reference Mixture V.

Example 14

In this example, a mercaptosilane according to the invention in which the alkyl part of the alkyl polyether groups has a certain minimum length of 11 C units is compared with a mercaptosilane in which the alkyl part of the alkyl polyether groups does not have this minimum length, with a simultaneously increased length of the polyether part.

Example Mixture I comprises the silane according to the invention from Example 1.

The silane used for Reference Mixture VII is the mercaptosilane from Example 7 of the general formula IV, where $R^{12}$=ethoxy and $R^{14}$=alkyl polyether groups —O—($CH_2$—$CH_2$—O)$_m$—$C_nH_{2n+1}$ where m is on average 20, n=10 and p=1.1.

The recipe used for the rubber mixtures is given in the following Table 7. In this context, the unit phr again means parts by weight per 100 parts of the crude rubber employed.

TABLE 7

| Substance | Amount [phr] Example Mixture 1 | Amount [phr] Reference Mixture VII |
|---|---|---|
| 1st stage | | |
| Buna VSL 5025-1 | 96 | 96 |
| Buna CB 24 | 30 | 30 |
| Ultrasil 7000 GR | 80 | 80 |
| ZnO | 3 | 3 |
| Stearic acid | 2 | 2 |
| Naftolen ZD | 10 | 10 |
| Vulkanox 4020 | 1.5 | 1.5 |
| Protector G 3108 | 1 | 1 |
| Silane from Example 1 | 10 | — |
| Silane from Example 7 | — | 10 |
| 2nd stage Batch stage 1 | | |
| 3rd stage Batch stage 2 | | |
| Vulkacit D | 0.25 | 0.25 |
| Perkacit TBzTD | 0.5 | 0.5 |
| Vulkacit CZ | 1.5 | 1.5 |
| Sulfur | 2.2 | 2.2 |

The rubber mixture is prepared in three stages in an internal mixer in accordance with Table 2.

The rubber testing is carried out in accordance with the test methods described in Table 3.

The rubber data for the crude mixture and vulcanisate are given in Table 8.

TABLE 8

| Feature: | Unit: | Example Mixture 1 | Reference Mixture VII |
|---|---|---|---|
| Crude mixture data | | | |
| ML(1 + 4) at 100° C., 3rd stage | [MU] | 65 | 76 |
| Dmax − Dmin | [dNm] | 17.9 | 29.3 |
| t 10% | [min] | 1.2 | 0.5 |
| t 80% − t 20% | [min] | 1.1 | 1.5 |
| Scorch time, t5 | [min] | 9.13 | 12.30 |
| Scorch time, t35 | [min] | 14.07 | 16.00 |
| Vulcanisate data | | | |
| Tensile strength | [MPa] | 14.7 | 13.9 |
| Modulus 100% | [MPa] | 2.1 | 2.1 |
| Modulus 300% | [MPa] | 12.2 | 9.8 |
| Modulus 300%/100% | [—] | 5.8 | 4.7 |
| Elongation at break | [%] | 340 | 385 |
| Shore A hardness | [SH] | 61 | 66 |
| Ball rebound, 60° C. | [%] | 73.3 | 67.2 |
| DIN abrasion | [mm$^3$] | 77 | 114 |
| Dyn. extension modulus E* 0° C. | [MPa] | 11.2 | 17.2 |
| Dyn. extension modulus E* 60° C. | [MPa] | 7.6 | 10.3 |
| Loss factor tan δ, 0° C. | [—] | 0.317 | 0.336 |
| Loss factor tan δ, 60° C. | [—] | 0.064 | 0.074 |

It is found again that only Example Mixture I provides a balanced profile of values. In addition to the high Mooney viscosity and the high Dmax–Dmin value, Reference Mixture VII shows a very short t10% time. Acceptable processing of this reference mixture cannot be ensured. In addition, Reference Mixture VII does not achieve the high level of Example Mixture I in the vulcanisate data. In addition to the low amplification factor (modulus 300%/100%) and the low ball rebound, the poor DIN abrasion is striking above all. Compared with the example mixture, this is increased by 48%. A lengthening of the polyether part of the alkyl polyether groups (m=5 for the silane from Example 1 compared with m=20 for the silane from Example 7) thus does not lead to achievement of the object according to the invention of providing mercaptosilanes which, with economically acceptable short mixing times and ensured processing, also lead to a high amplification ratio, a low hysteresis loss and a high abrasion resistance, with at the same time a reduced emission of alcohol compared with trimethoxy- and triethoxy-substituted mercaptosilanes.

Example 15

Mercaptosilanes of the general formula I according to the invention with different degrees of transesterification, i.e. with differences in the substituents $R^2$, are used in this example.

The silane according to the invention used for Example Mixture II is the mercaptosilane prepared in Example 8. Its structure corresponds to the general formula I, wherein $R^1$ is an alkyl polyether group —O—(CH$_2$—CH$_2$—O)$_m$—C$_n$H$_{2n+1}$, where m is on average 5 and n is 13, $R^2$ is ethoxy CH$_3$CH$_2$O—, $R^3$ is the trimethylene group —CH$_2$—CH$_2$—CH$_2$— and $R^4$ is H.

The silane according to the invention used for Example Mixture III is the mercaptosilane prepared in Example 9. Its structure corresponds to the general formula I, wherein $R^1$ is an alkyl polyether group —O—(CH$_2$—CH$_2$—O)$_m$—C$_n$H$_{2n+1}$, where m is on average 5 and n is 13, $R^2$ is a mixture of $R^1$ and ethoxy CH$_3$CH$_2$O— in the ratio of 1:1, $R^3$ is the trimethylene group —CH$_2$—CH$_2$—CH$_2$— and $R^4$ is H.

The silane according to the invention used for Example Mixture IV is the mercaptosilane prepared in Example 10. Its structure corresponds to the general formula I, wherein $R^1$ is an alkyl polyether group —O—(CH$_2$—CH$_2$—O)$_m$—C$_n$H$_{2n+1}$, where m is on average 5 and n is 13, $R^2$ is $R^1$, $R^3$ is the trimethylene group —CH$_2$—CH$_2$—CH$_2$— and $R^4$ is H.

Si 69 is used for Reference Mixture VIII.

The silane used for Reference Mixture IX is again the silane from Example 2.

The recipe used for the rubber mixtures is given in the following Table 9. In this context, the unit phr again means parts by weight per 100 parts of the crude rubber employed. The mercaptosilanes used are metered into Example Mixtures II to IV according to the invention and Reference Mixture IX in isomolar amounts.

TABLE 9

| Substance | Amount [phr] Example Mixture II | Amount [phr] Example Mixture III | Amount [phr] Example Mixture IV | Amount [phr] Reference Mixture VIII | Amount [phr] Reference Mixture IX |
|---|---|---|---|---|---|
| 1st stage | | | | | |
| Buna VSL 5025-1 | 96 | 96 | 96 | 96 | 96 |
| Buna CB 24 | 30 | 30 | 30 | 30 | 30 |
| Ultrasil 7000GR | 80 | 80 | 80 | 80 | 80 |
| ZnO | 3 | 3 | 3 | 3 | 3 |
| Stearic acid | 2 | 2 | 2 | 2 | 2 |
| Naftolen ZD | 10 | 10 | 10 | 10 | 10 |
| Vulkanox 4020 | 1.5 | 1.5 | 1.5 | 1.5 | 1.5 |
| Protector G3108 | 1 | 1 | 1 | 1 | 1 |
| Silane from Example 8 | 6.2 | — | — | — | — |
| Silane from Example 9 | — | 10 | — | — | — |
| Silane from Example 10 | — | — | 13.8 | — | — |

TABLE 9-continued

| Substance | Amount [phr] Example Mixture II | Amount [phr] Example Mixture III | Amount [phr] Example Mixture IV | Amount [phr] Reference Mixture VIII | Amount [phr] Reference Mixture IX |
|---|---|---|---|---|---|
| Si 69 | — | — | — | 6.4 | — |
| Silane from Example 2 | — | — | — | — | 5.4 |
| 2nd stage Batch stage 1 | | | | | |
| 3rd stage Batch stage 2 | | | | | |
| Vulkacit D | 0.25 | 0.25 | 0.25 | 2 | 0.25 |
| Perkacit TBzTD | 0.5 | 0.5 | 0.5 | 0.2 | 0.5 |
| Vulkacit CZ | 1.5 | 1.5 | 1.5 | 1.5 | 1.5 |
| Sulfur | 2.2 | 2.2 | 2.2 | 1.5 | 2.2 |

The rubber mixture is prepared in three stages in an internal mixer in accordance with Table 2.

The rubber testing is carried out in accordance with the test methods described in Table 3.

The rubber data for the crude mixture and vulcanisate are given in Table 10.

example mixtures have advantages in the vulcanisate properties compared with the two reference mixtures. The tan δ value at 60° C. is reduced significantly in all of them, and the ball rebound is increased significantly in all of them. The DIN abrasion is also at a low level in all the three example mixtures. It is therefore to be assumed, regardless of the

TABLE 10

| Feature: | Unit: | Example Mixture II | Example Mixture III | Example Mixture IV | Reference Mixture VIII | Reference Mixture IX |
|---|---|---|---|---|---|---|
| Crude mixture data | | | | | | |
| ML(1 + 4) at 100° C., 3rd stage | [MU] | 65 | 60 | 61 | 66 | 83 |
| Dmax – Dmin | [dNm] | 21.1 | 18.8 | 15.9 | 18.7 | 29.9 |
| t 10% | [min] | 1.4 | 1.4 | 1.1 | 1.5 | 0.4 |
| t 80% – t 20% | [min] | 1.5 | 1.3 | 1.1 | 3.2 | 1.8 |
| Scorch time, t5 | [min] | 15.9 | 12.0 | 6.2 | 31.3 | 16.5 |
| Scorch time, t35 | [min] | 20.6 | 16.9 | 11.3 | 42.4 | 19.1 |
| Vulcanisate data | | | | | | |
| Tensile strength | [MPa] | 12.7 | 13.3 | 11.9 | 12.4 | 14.4 |
| Modulus 100% | [MPa] | 2.0 | 2.0 | 2.0 | 1.7 | 1.8 |
| Modulus 300% | [MPa] | 11.5 | 11.6 | — | 8.5 | 9.2 |
| Modulus 300%/100% | [—] | 5.8 | 5.8 | — | 5.0 | 5.1 |
| Elongation at break | [%] | 315 | 330 | 295 | 380 | 395 |
| Shore A hardness | [SH] | 62 | 61 | 59 | 63 | 67 |
| Ball rebound, 60° C. | [%] | 70.3 | 72.5 | 75.0 | 64.5 | 68.4 |
| DIN abrasion | [mm$^3$] | 73 | 79 | 65 | 88 | 79 |
| Dyn. extension modulus E* 0° C. | [MPa] | 15.6 | 12.9 | 10.4 | 21.5 | 26.7 |
| Dyn. extension modulus E* 60° C. | [MPa] | 8.5 | 8.1 | 7.5 | 9.7 | 12.6 |
| Loss factor tan δ, 0° C. | [—] | 0.390 | 0.362 | 0.288 | 0.426 | 0.333 |
| Loss factor tan δ, 60° C. | [—] | 0.083 | 0.076 | 0.068 | 0.130 | 0.104 |

Reference mixture VIII is prepared with the commercially available Si 69. Under the mixing conditions used here, Reference Mixture IX prepared with the mercaptosilane according to the prior art, which is not according to the invention, indeed shows advantages in the vulcanisate data compared with Reference Mixture VIII, but the poorer values in the crude mixture data, above all the significantly increased Mooney viscosity and the extremely short t10% time, show that this mixture cannot be processed commercially. Only the example mixtures prepared with the mercaptosilanes according to the invention are all commercially processable. The t10% times are of the order of Reference Mixture VIII. The Mooney viscosities are even reduced further, compared with Reference Mixture VIII. All the degrees of transesterification, that a tyre with a tread based on rubber mixtures comprising the mercaptosilanes according to the invention has significant advantages in rolling resistance and abrasion compared with the prior art.

Example 16

It is shown in this example that the organosilane can be a mixture of various silanes corresponding to the formula I or condensation products thereof and leads to advantageous rubber values. Example Mixture V comprises the silane according to the invention from Example 1. Example Mixture VI comprises the silane according to the invention from Example 11. The silane according to the invention from Example 11 corresponds to a mixture of a silane of which the structure corresponds to the general formula I, wherein $R^1$ is an alkyl polyether group $—O—(CH_2—CH_2—O)_m—C_nH_{2n+1}$, where m is on average 5 and n is 13, $R^2$ is a mixture of $R^1$ and ethoxy groups in the ratio of 1.5:0.5, $R^3$ is the trimethylene group $—CH_2—CH_2—CH_2—$ and $R^4$ is H, and condensation products thereof in the ratio of approx. 70:30. The recipe used for the rubber mixtures is shown in the following Table 11. In this context, the unit phr again means parts by weight per 100 parts of the crude rubber employed.

TABLE 11

| Substance | Amount [phr] Example Mixture V | Amount [phr] Example Mixture VI |
|---|---|---|
| 1st stage | | |
| Buna VSL 5025-1 | 96 | 96 |
| Buna CB 24 | 30 | 30 |
| Ultrasil 7000 GR | 80 | 80 |
| ZnO | 3 | 3 |
| Stearic acid | 2 | 2 |
| Naftolen ZD | 10 | 10 |
| Vulkanox 4020 | 1.5 | 1.5 |
| Protector G 3108 | 1 | 1 |
| Silane from Example 1 | 9.97 | — |
| Silane from Example 11 | — | 9.97 |
| 2nd stage | | |
| Batch stage 1 | | |
| 3rd stage | | |
| Batch stage 2 | | |
| Vulkacit D | 0.25 | 0.25 |
| Perkacit TBzTD | 0.5 | 0.5 |
| Vulkacit CZ | 1.5 | 1.5 |
| Sulfur | 2.2 | 2.2 |

The rubber mixture is prepared in three stages in an internal mixer in accordance with Table 2.

The rubber testing is carried out in accordance with the test methods described in Table 3.

The rubber data for the crude mixture and vulcanisate are given in Table 12.

TABLE 12

| Feature: | Unit: | Example Mixture V | Example Mixture VI |
|---|---|---|---|
| Crude mixture data | | | |
| ML(1 + 4) at 100° C., 3rd stage | [MU] | 63 | 66 |
| Dmax − Dmin | [dNm] | 23.1 | 23.8 |
| t 10% | [min] | 1.1 | 1.1 |
| t 80% − t 20% | [min] | 1.4 | 1.7 |
| Scorch time, t5 | [min] | 12.88 | 22.95 |
| Scorch time, t35 | [min] | 18.24 | 27.79 |
| Vulcanisate data | | | |
| Tensile strength | [MPa] | 13.2 | 13.0 |
| Modulus 100% | [MPa] | 2.0 | 2.0 |
| Modulus 300% | [MPa] | 10.5 | 9.9 |
| Modulus 300%/100% | [—] | 5.3 | 5.0 |
| Elongation at break | [%] | 345 | 360 |
| Shore A hardness | [SH] | 63 | 65 |

TABLE 12-continued

| Feature: | Unit: | Example Mixture V | Example Mixture VI |
|---|---|---|---|
| Ball rebound, 60° C. | [%] | 70.0 | 69.9 |
| DIN abrasion | [mm³] | 81 | 87 |
| Dyn. extension modulus E* 0° C. | [MPa] | 12.7 | 14.2 |
| Dyn. extension modulus E* 60° C. | [MPa] | 8.4 | 9.1 |
| Loss factor tan δ, 0° C. | [—] | 0.334 | 0.332 |
| Loss factor tan δ, 60° C. | [—] | 0.074 | 0.077 |

Table 12 shows that the two example mixtures give virtually identical values. The amplification level and the tan δ are also at a high level in Example Mixture VI, as in Example Mixture V. The only significant difference lies in the scorch time. Example Mixture VI with the silane according to the invention from Example 11 even shows a significant advantage here. The prolonged scorch time shows that the scorch safety is increased here, which is advantageous for the processing of rubber mixtures.

A mixture of various silanes corresponding to formula I or condensation products thereof is therefore a preferred embodiment of the invention.

Example 17

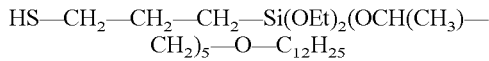

$$HS—CH_2—CH_2—CH_2—Si(OEt)_2(OCH(CH_3)—CH_2)_5—O—C_{12}H_{25}$$

79.5 g HS—CH₂—CH₂—CH₂—Si(OEt)₃, 158.7 g polypropylene glycol monododecyl ether (H—(OCH(CH₃)—CH₂)₅—O—C₁₂H₂₅ (Schärer & Schläpfer AG)) and 0.05 g Ti(OBu)₄ are mixed in a vacuum distillation apparatus. The mixture is heated to 141° C. and the pressure is lowered from 600 mbar to 100 mbar in the course of 5.5 h. The volatile alcohol liberated is distilled off. The mixture is then heated at 141° C. under 80 mbar for 4 h. When the reaction has ended, the product obtained is cooled to room temperature.

The weight of the product isolated is 217.4 g.

An average degree of transesterification of 1 is determined by ¹³C-NMR spectroscopy (35% Si—(OCH(CH₃)—CH₂)₅—O—C₁₂H₂₅ vs. 65% Si—OEt functionalities).

Example 18

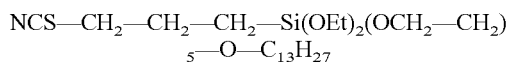

$$NCS—CH_2—CH_2—CH_2—Si(OEt)_2(OCH_2—CH_2)_5—O—C_{13}H_{27}$$

100 g NCS—CH₂—CH₂—CH₂—Si(OEt)₃, 161.4 g polyethylene glycol monotridecyl ether (H—(OCH₂—CH₂)₅—O—C₁₃H₂₇, Lutensol TO 5 (BASF AG)) and 0.05 g Ti(OBu)₄ are mixed in a vacuum distillation apparatus. The mixture is heated to 146° C. and the pressure is lowered from 600 mbar to 100 mbar in the course of 4 h. The volatile alcohol liberated is distilled off. The mixture is then heated at 141° C. under 50 mbar for 6 h. When the reaction has ended, the product obtained is cooled to room temperature.

The weight of the product is 239 g.

An average degree of transesterification of 1 is determined by ¹³C-NMR spectroscopy (30.6% Si—(OCH₂—CH₂)₅—O—C₁₂H₂₅ vs. 69.4% Si—OEt functionalities).

Example 19

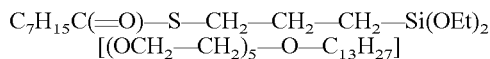
[(OCH$_2$—CH$_2$)$_5$—O—C$_{13}$H$_{27}$]

150 g HS—CH$_2$—CH$_2$—CH$_2$—Si(OEt)$_2$(OCH$_2$—CH$_2$)$_5$—O—C$_{13}$H$_{27}$ and 500 ml heptane are initially introduced into a four-necked flask with a reflux condenser under an inert gas at 5° C. 26.3 g triethylamine are then slowly added dropwise. After the dropwise addition the mixture is stirred at 5° C. for 10 min and 38.3 g octanoyl chloride are then slowly added dropwise such that the internal temperature does not rise above 8° C. The suspension is stirred at 5-20° C. for 90 min and then boiled under reflux for 90 min. The suspension is cooled and the solid is filtered off. The salt which has been separated off is washed with 100 ml heptane. The entire filtrate is freed from the solvent at 65° C. on a rotary evaporator. The weight of the product is 161.3 g.

An average degree of transesterification of 1 is determined by $^{13}$C-NMR spectroscopy (32% Si—(OCH$_2$—CH$_{12}$)$_5$—O—C$_{13}$H$_{27}$ vs. 68% Si—OEt functionalities).

Example 20

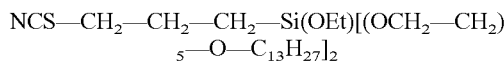
$_5$—O—C$_{13}$H$_{27}$]$_2$ 101 g NCS—CH$_2$—CH$_2$—CH$_2$—Si(OEt)$_3$, 322.5 g polyethylene glycol monotridecyl ether (H—(OCH$_2$—CH$_2$)$_5$—O—C$_{13}$H$_{27}$, Lutensol TO 5 (BASF AG)) and 0.05 g Ti(OBu)$_4$ are mixed in a vacuum distillation apparatus. The mixture is heated to 144° C. and the pressure is lowered from 800 mbar to 100 mbar in the course of 4 h. The volatile alcohol liberated is distilled off. The mixture is then heated at 144° C. under 50 mbar for 6 h. When the reaction has ended, the product obtained is cooled to room temperature. The weight of the product is 376.6 g.

An average degree of transesterification of 2 is determined by $^{13}$C-NMR spectroscopy (66% Si—(OCH$_2$—CH$_2$)$_5$—O—C$_{12}$H$_{25}$ vs. 34% Si—OEt functionalities).

Example 21

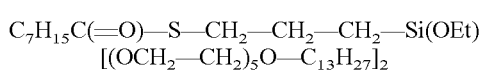
[(OCH$_2$—CH$_2$)$_5$O—C$_{13}$H$_{27}$]$_2$ 200 g HS—CH$_2$—CH$_2$—CH$_2$—Si(OEt)[(OCH$_2$—CH$_2$)$_5$—O—C$_{13}$H$_{27}$]$_2$ and 500 ml heptane are initially introduced into a four-necked flask with a reflux condenser under an inert gas at 5° C. 22.3 g triethylamine are then slowly added dropwise. After the dropwise addition the mixture is stirred at 5° C. for 10 min and 32.7 g octanoyl chloride are then slowly added dropwise such that the internal temperature does not rise above 8° C. The suspension is stirred at 5-20° C. for 90 min and then boiled under reflux for 90 min. The suspension is cooled and the solid is filtered off. The salt which has been separated off is washed with 100 ml heptane. The entire filtrate is freed from the solvent at 65° C. on a rotary evaporator.
The weight of the product is 211.4 g.

An average degree of transesterification of 2 is determined for the product by $^{13}$C-NMR spectroscopy (67% Si—(OCH$_2$—CH$_2$)$_5$—O—C$_{13}$H$_{27}$ vs. 33% Si—OEt functionalities).

Example 22

Silanes of the general formula I according to the invention having substituted mercapto groups, i.e. where R$^4$ is CN or (C=O)—R$^9$, which are substituted by an alkyl polyether group on the silicon, are employed in this example.

Example Mixture VII, comprising the silane according to the invention from Example 18, and Example Mixture VIII, comprising the silane according to the invention from Example 19, are compared with mixtures comprising silanes which correspond to the prior art.

Si 69 is used for Reference Mixture X. The silane used for Reference Mixture XI is again the silane from Example 2.

The recipe used for the rubber mixtures is given in the following Table 13. In this context, the unit phr again means parts by weight per 100 parts of the crude rubber employed.

TABLE 13

| Substance | Amount [phr] Reference Mixture X | Amount [phr] Reference Mixture XI | Amount [phr] Example Mixture VII | Amount [phr] Example Mixture VIII |
|---|---|---|---|---|
| 1st stage | | | | |
| Buna VSL 5025-1 | 96 | 96 | 96 | 96 |
| Buna CB 24 | 30 | 30 | 30 | 30 |
| Ultrasil 7000GR | 80 | 80 | 80 | 80 |
| ZnO | 3 | 3 | 3 | 3 |
| Stearic acid | 2 | 2 | 2 | 2 |
| Naftolen ZD | 10 | 10 | 10 | 10 |
| Vulkanox 4020 | 1.5 | 1.5 | 1.5 | 1.5 |
| Protector G3108 | 1 | 1 | 1 | 1 |
| Si 69 | 6.4 | — | — | — |
| Silane from Example 2 | — | 6.4 | — | — |
| Silane from Example 18 | — | — | 6.4 | — |
| Silane from Example 19 | — | — | — | 6.4 |
| 2nd stage Batch stage 1 | | | | |
| 3rd stage Batch stage 2 | | | | |
| Vulkacit D | 2 | 0.25 | 0.25 | 0.25 |
| Perkacit TBzTD | 0.2 | 0.5 | 0.5 | 0.5 |
| Vulkacit CZ | 1.5 | 1.5 | 1.5 | 1.5 |
| Sulfur | 1.5 | 2.2 | 2.2 | 2.2 |

The rubber mixture is prepared in three stages in an internal mixer in accordance with Table 2.

The rubber testing is carried out in accordance with the test methods described in Table 3. The results are shown in Table 14.

TABLE 14

| Feature: | Unit | Reference Mixture X | Reference Mixture XI | Example Mixture VII | Example Mixture VIII |
|---|---|---|---|---|---|
| Crude mixture data | | | | | |
| ML(1 + 4) at 100° C., 3rd stage | [MU] | 74 | 96 | 85 | 84 |

TABLE 14-continued

| Feature: | Unit | Reference Mixture X | Reference Mixture XI | Example Mixture VII | Example Mixture VIII |
|---|---|---|---|---|---|
| Dmax − Dmin | [dNm] | 18.79 | 22.92 | 22.83 | 28.25 |
| t 10% | [min] | 1.21 | 0.66 | 0.46 | 0.54 |
| t 80% − t 20% | [min] | 3.41 | 2.07 | 1.94 | 2.51 |
| Scorch time, t5 | [min] | 31.55 | 6.00 | 37.33 | 43.73 |
| Scorch time, t35 | [min] | 43.78 | 8.08 | 43.21 | 49.27 |
| Vulcanisate data | | | | | |
| Tensile strength | [MPa] | 13.70 | 11.40 | 12.70 | 11.60 |
| Modulus 100% | [MPa] | 1.80 | 1.90 | 2.10 | 2.10 |
| Modulus 300% | [MPa] | 8.90 | 10.60 | 9.70 | 9.10 |
| Modulus 300%/100% | [—] | 4.94 | 5.58 | 4.62 | 4.33 |
| Elongation at break | [%] | 398 | 308 | 356 | 357 |
| Shore A hardness | [SH] | 65 | 61 | 69 | 70 |
| Ball rebound, 60° C. | [%] | 61.1 | 70.3 | 65.1 | 63.7 |
| DIN abrasion | [mm$^3$] | 99 | 61 | 104 | 111 |
| Dyn. extension modulus E*, 0° C. | [MPa] | 22.4 | 14.2 | 26.3 | 26.9 |
| Dyn. extension modulus E*, 60° C. | [MPa] | 13.0 | 11.8 | 15.8 | 15.8 |
| Loss factor tan δ, 0° C. | [—] | 0.525 | 0.412 | 0.449 | 0.442 |
| Loss factor tan δ, 60° C. | [—] | 0.120 | 0.085 | 0.096 | 0.094 |

It is found again that under the mixing conditions used here, Reference Mixture XI prepared with the mercaptosilane according to the prior art, which is not according to the invention, indeed has advantages in the vulcanisate data compared with Reference Mixture X prepared with the commercially available Si 69, but, as the extremely short Mooney scorch time shows, cannot be processed commercially. Only Example Mixtures VII and VIII prepared with the silanes according to the invention have a high potential of the vulcanisate data with simultaneously ensured processing. The Mooney scorch times are in the range of Reference Mixture X prepared with the commercially available Si 69. Example Mixture VIII even exceeds these. The DIN abrasion and modulus 300% likewise coincide with those of Reference Mixture X, while the low value for tan δ, 60° C. shows the reduced hysteresis loss.

Example 23

Silanes of the general formula I according to the invention having substituted mercapto groups, i.e. where $R^4$ is CN or (C=O)—$R^9$, which are substituted by two alkyl polyether groups on the silicon, are employed in this example.

Example Mixture IX, comprising the silane according to the invention from Example 20, and Example Mixture X, comprising the silane according to the invention from Example 21, are compared with mixtures comprising silanes which correspond to the prior art.

Si 69 is used for Reference Mixture XII. The silane used for Reference Mixture XIII is again the silane from Example 2.

The recipe used for the rubber mixtures is given in the following Table 15. In this context, the unit phr again means parts by weight per 100 parts of the crude rubber employed.

TABLE 15

| Substance | Amount [phr] Reference Mixture XII | Amount [phr] Reference Mixture XIII | Amount [phr] Example Mixture IX | Amount [phr] Example Mixture X |
|---|---|---|---|---|
| 1st stage | | | | |
| Buna VSL 5025-1 | 96 | 96 | 96 | 96 |
| Buna CB 24 | 30 | 30 | 30 | 30 |
| Ultrasil 7000GR | 80 | 80 | 80 | 80 |
| ZnO | 3 | 3 | 3 | 3 |
| Stearic acid | 2 | 2 | 2 | 2 |
| Naftolen ZD | 10 | 10 | 10 | 10 |
| Vulkanox 4020 | 1.5 | 1.5 | 1.5 | 1.5 |
| Protector G3108 | 1 | 1 | 1 | 1 |
| Si 69 | 10 | — | — | — |
| Silane from Example 2 | — | 10 | — | — |
| Silane from Example 20 | — | — | 10 | — |
| Silane from Example 21 | — | — | — | 10 |
| 2nd stage | | | | |
| Batch stage 1 | | | | |
| 3rd stage | | | | |
| Batch stage 2 | | | | |
| Vulkacit D | 2 | 0.25 | 0.25 | 0.25 |
| Perkacit TBzTD | 0.2 | 0.5 | 0.5 | 0.5 |
| Vulkacit CZ | 1.5 | 1.5 | 1.5 | 1.5 |
| Sulfur | 1.5 | 2.2 | 2.2 | 2.2 |

The rubber mixture is prepared in three stages in an internal mixer in accordance with Table 2.

The rubber testing is carried out in accordance with the test methods described in Table 3. The results are shown in Table 16.

TABLE 16

| Feature: | Unit: | Reference Mixture XII | Reference Mixture XIII | Example Mixture IX | Example Mixture X |
|---|---|---|---|---|---|
| Crude mixture data | | | | | |
| ML(1 + 4) at 100° C., 3rd stage | [MU] | 66 | 99 | 65 | 65 |
| Dmax − Dmin | [dNm] | 21.61 | 14.85 | 23.53 | 24.83 |
| t 10% | [min] | 1.40 | 0.56 | 1.78 | 1.73 |
| t 80% − t 20% | [min] | 3.39 | 5.47 | 1.87 | 2.56 |
| Scorch time, t5 | [min] | 26.15 | 2.67 | 49.16 | 47.70 |
| Scorch time, t35 | [min] | 34.32 | 4.39 | 55.29 | 55.53 |
| Vulcanisate data | | | | | |
| Tensile strength | [MPa] | 9.20 | 9.00 | 11.90 | 11.10 |
| Modulus 100% | [MPa] | 2.40 | 1.80 | 1.90 | 2.10 |
| Modulus 300% | [MPa] | — | — | 8.90 | 9.30 |
| Modulus 300%/100% | [—] | — | — | 4.68 | 4.43 |
| Elongation at break | [%] | 256 | 256 | 367 | 340 |
| Shore A hardness | [SH] | 68 | 56 | 66 | 68 |
| Ball rebound, 60° C. | [%] | 62.5 | 73.1 | 65.6 | 64.5 |
| DIN abrasion | [mm³] | 93 | 55 | 104 | 113 |
| Dyn. extension modulus E*, 0° C. | [MPa] | 27.2 | 11.1 | 16.5 | 17.3 |
| Dyn. extension modulus E*, 60° C. | [MPa] | 15.6 | 12.4 | 15.9 | 16.5 |
| Loss factor tan δ, 0° C. | [—] | 0.495 | 0.381 | 0.449 | 0.447 |
| Loss factor tan δ, 60° C. | [—] | 0.107 | 0.082 | 0.085 | 0.095 |

The known pattern emerges again. Under the mixing conditions used here, Reference Mixture XIII prepared with the mercaptosilane according to the prior art, which is not according to the invention, indeed has advantages in the vulcanisate data compared with Reference Mixture XII prepared with the commercially available Si 69, but with the amount employed used in this comparison also cannot be processed commercially. The high Mooney viscosity and the extremely short scorch times suggest problems during mixing and extrusion, while it can be concluded from the short t10% times that vulcanization is made difficult. The crude mixture data of Example Mixtures IX and X according to the invention are at the level of Reference Mixture XII prepared with the commercially available Si 69, or even exceed these in Mooney scorch times. Processability on a large industrial scale is ensured. The vulcanisate data of Example Mixtures IX and X again have a high potential compared with Reference Mixture XII, and with the reduced tan δ, 60° C. values show significant advantages in the hysteresis loss.

The invention claimed is:

1. A composition comprising a mixture of mercaptosilanes of the formula I,

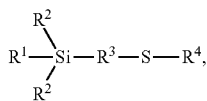

I wherein $R^1$ is an alkyl polyether group —O—($R^5$—O)$_m$—$R^6$, where $R^5$ is identical or different and is a branched or unbranched, saturated or unsaturated, aliphatic divalent C1-C30 hydrocarbon group, m is on average 3 to 10, and $R^6$ comprises at least 11 C atoms and is an unsubstituted or substituted, branched or unbranched monovalent alkyl, alkenyl, aryl or aralkyl group, wherein one $R^2$ is an ethoxy group and the other $R^2$ is an $R^1$, C1-C12 alkyl, or $R^7O$ group, where $R^7$ is H, methyl, ethyl, propyl, a C9-C30 branched or unbranched monovalent alkyl, alkenyl, aryl or aralkyl group or $(R^8)_3Si$ group, where $R^8$ is a C1-C30 branched or unbranched, alkyl or alkenyl group, $R^3$ is a branched or unbranched, saturated or unsaturated, aliphatic, aromatic or mixed aliphatic/aromatic divalent C1-C30 hydrocarbon group, and $R^4$ is H, CN or (C=O)—$R^9$, where $R^9$ is a branched or unbranched, saturated or unsaturated, aliphatic, aromatic or mixed aliphatic/aromatic monovalent C1-C30 hydrocarbon group.

2. The composition according to claim 1, wherein $R^1$ has a molecular weight distribution.

3. The composition according to claim 1, wherein $R^6$ is $C_{13}H_{27}$.

4. The composition according to claim 1, and further comprising

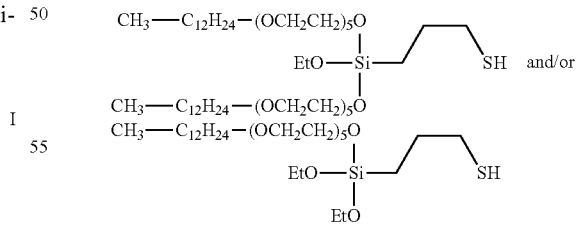

and/or hydrolysis and/or condensation products thereof.

5. The composition according to claim 1, wherein $R^2$ is a C1-C12 alkyl or $R^7O$ group, where $R^7$ is H, ethyl, propyl, a C9-C30 branched or unbranched monovalent alkyl, alkenyl, aryl or aralkyl group or $(R^8)_3Si$ group.

6. The composition according to claim 1, wherein $R^2$ is $R^1$, C1-C12-alkyl or $R^7O$ group and $R^1$ is a member selected from the group consisting of:

—O—(C$_2$H$_4$—O)$_5$—C$_{11}$H$_{23}$, —O—(C$_2$H$_4$—O)$_5$—C$_{12}$H$_{25}$, —O—(C$_2$H$_4$—O)$_5$—C$_{13}$H$_{27}$, —O—(C$_2$H$_4$—O)$_5$—C$_{14}$H$_{29}$, —O—(C$_2$H$_4$—O)$_5$—C$_{15}$H$_{31}$, —O—(C$_2$H$_4$—O)$_3$—C$_{13}$H$_{27}$, —O—(C$_2$H$_4$—O)$_4$—C$_{13}$H$_{27}$, —O—(C$_2$H$_4$—O)$_6$—C$_{13}$H$_{27}$, —O—(C$_2$H$_4$—O)$_7$—C$_{13}$H$_{27}$, —O—(CH$_2$CH$_2$—O)$_5$—(CH$_2$)$_{10}$CH$_3$, —O—(CH$_2$CH$_2$—O)$_5$—(CH$_2$)$_{11}$CH$_3$, —O—(CH$_2$CH$_2$—O)$_5$—(CH$_2$)$_{12}$CH$_3$, —O—(CH$_2$CH$_2$—O)$_5$—(CH$_2$)$_{13}$CH$_3$, —O—(CH$_2$CH$_2$—O)$_5$—(CH$_2$)$_{14}$CH$_3$, —O—(CH$_2$CH$_2$—O)$_3$—(CH$_2$)$_{12}$CH$_3$, —O—(CH$_2$CH$_2$—O)$_4$—(CH$_2$)$_{12}$CH$_3$, —O—(CH$_2$CH$_2$—O)$_6$—(CH$_2$)$_{12}$CH$_3$, —O—(CH$_2$CH$_2$—O)$_7$—(CH$_2$)$_{12}$CH$_3$,

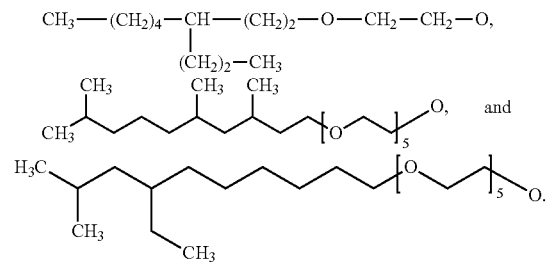

7. The composition according to claim 1, wherein R$^2$ is R$^1$- and R$^1$ is a member selected form the group consisting of —O—(C$_2$H$_4$—O)$_5$—C$_{11}$H$_{23}$, —O—(C$_2$H$_4$—O)$_5$—C$_{12}$H$_{25}$, —O—(C$_2$H$_4$—O)$_5$—C$_{13}$H$_{27}$, —O—(C$_2$H$_4$—O)$_5$—C$_{14}$H$_{29}$, —O—(C$_2$H$_4$—O)$_5$—C$_{15}$H$_{31}$, —O—(C$_2$H$_4$—O)$_3$—C$_{13}$H$_{27}$, —O—(C$_2$H$_4$—O)$_4$—C$_{13}$H$_{27}$, —O—(C$_2$H$_4$—O)$_6$—C$_{13}$H$_{27}$, —O—(C$_2$H$_4$—O)$_7$—C$_{13}$H$_{27}$, —O—(CH$_2$CH$_2$—O)$_5$—(CH$_2$)$_{10}$CH$_3$, —O—(CH$_2$CH$_2$—O)$_5$—(CH$_2$)$_{11}$CH$_3$, —O—(CH$_2$CH$_2$—O)$_5$—(CH$_2$)$_{12}$CH$_3$, —O—(CH$_2$CH$_2$—O)$_5$—(CH$_2$)$_{13}$CH$_3$, —O—(CH$_2$CH$_2$—O)$_5$—(CH$_2$)$_{14}$CH$_3$, —O—(CH$_2$CH$_2$—O)$_3$—(CH$_2$)$_{12}$CH$_3$, —O—(CH$_2$CH$_2$—O)$_4$—(CH$_2$)$_{12}$CH$_3$, —O—(CH$_2$CH$_2$—O)$_6$—(CH$_2$)$_{12}$CH$_3$, —O—(CH$_2$CH$_2$—O)$_7$—(CH$_2$)$_{12}$CH$_3$,

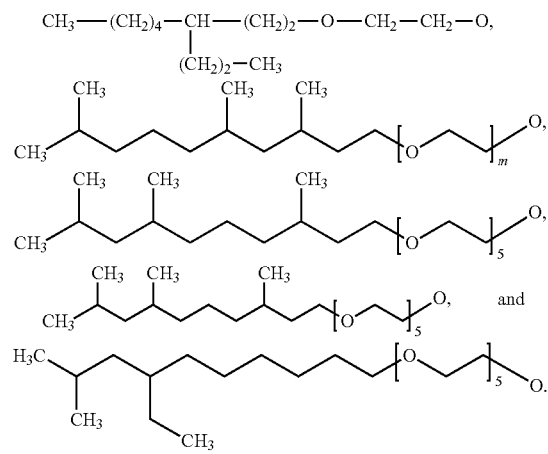

8. An inert organic or inorganic support having absorbed therein a composition according to claim 1.

9. An organic or inorganic support having been pre-reacted with a composition according to claim 1.

10. A process for the preparation of a composition according to claim 1, wherein at least one silane of the formula II

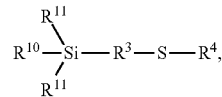

wherein R$^{10}$ is an R$^7$O group and R$^7$ has the abovementioned meaning,

R$^{11}$ is identical or different and is an R$^{10}$ or C1-C12-alkyl group,

R$^3$ and R$^4$ have the abovementioned meaning, is catalytically reacted with an alkoxylated alcohol R$^1$—H, wherein R$^1$ has the abovementioned meaning, splitting R$^7$—OH off, and separating R$^7$—OH off from the reaction mixture continuously or discontinuously.

11. The process according to claim 10, wherein the alkoxylated alcohol R$^1$—H is an ethoxylated alcohol.

12. The process according to claim 10, wherein the alkoxylated alcohol R$^1$—H is a propoxylated alcohol.

13. A rubber composition comprising:
(A) a rubber or a mixture of rubbers,
(B) a filler, and
(C) a composition according to claim 1.

14. The rubber composition according to claim 13, further comprising:
(D) a thiuram sulfide and/or carbamate accelerator and/or the corresponding zinc salts,
(E) a nitrogen-containing co-activator,
(F) optionally further rubber auxiliaries, and
(G) optionally further accelerators,
and the weight ratio of accelerator (D) to nitrogen-containing co-activator (E) is equal to or greater than 1.

15. A process for the preparation of the rubber composition, which comprises mixing rubber or a mixture of rubbers, a filler, optionally further rubber auxiliaries and a composition according to claim 1 in a mixing unit.

16. The process according to claim 15, and further comprising adding a thiuram sulfide and/or carbamate accelerator and/or the corresponding zinc salts, a nitrogen-containing co-activator, optionally adding a rubber auxiliary, and optionally adding an accelerator,
wherein the weight ratio of the accelerator to the nitrogen-containing co-activator is equal to or greater than 1.

17. A shaped article containing a composition according to claim 1.

18. The shaped article according to claim 17 which is a pneumatic tires, tire tread, cable sheathing, hose, drive belt, conveyor belt, roller covering, tire, shoe sole, sealing ring or damping element.

19. A mercaptosilane of the formula I,

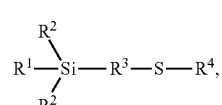

wherein R$^1$ is an alkyl polyether group —O—(R$^5$—O)$_m$—R$^6$, where R$^5$ is identical or different and is a branched or unbranched, saturated or unsaturated, aliphatic divalent C1-C30 hydrocarbon group, m is on average 3 to 10, and R$^6$ comprises at least 11 C atoms and is an unsubstituted or substituted, branched or unbranched monovalent alkyl, alkenyl, aryl or aralkyl group, $R^2$ is identical or different and is an $R^1$, C1-C12 alkyl or $R^7O$ group, where $R^7$ is H, methyl, ethyl, propyl, a C9-C30 branched or unbranched monovalent alkyl, alkenyl, aryl or aralkyl group or $(R^8)_3Si$ group, where $R^8$ is a C1-C30 branched or unbranched, alkyl or alkenyl group, $R^3$ is a branched or unbranched, saturated or unsaturated, aliphatic, aromatic or mixed aliphatic/aromatic divalent C1-C30 hydrocarbon group, and $R^4$ is H, CN or (C=O)—$R^9$, where $R^9$ is a branched or unbranched, saturated or unsaturated, aliphatic, aromatic or mixed aliphatic/aromatic monovalent C1-C30 hydrocarbon group.

20. A composition comprising a mixture of mercaptosilanes of the formula I according to claim 19 wherein $R^1$ has a molecular weight distribution.

21. The mercaptosilane according to claim 19, wherein m is on average 5.

* * * * *